United States Patent
Reis et al.

(10) Patent No.: US 9,687,447 B2
(45) Date of Patent: Jun. 27, 2017

(54) METHOD FOR PREPARING LIPOSOME-BASED CONSTRUCTS

(75) Inventors: Pedro Reis, Epalinges (CH); David Hickman, Saint-Sulpice (CH); Maria Pihlgren Bosch, Mont-sur-Lausanne (CH); Andreas Muhs, Cugy (CH); Andrea Pfeifer, St-Legier (CH)

(73) Assignee: AC Immune S.A., Lausanne (CH)

( * ) Notice: Subject to any disclaimer, the term of this patent is extended or adjusted under 35 U.S.C. 154(b) by 490 days.

(21) Appl. No.: 13/881,502

(22) PCT Filed: Oct. 26, 2011

(86) PCT No.: PCT/EP2011/068797
§ 371 (c)(1),
(2), (4) Date: Apr. 25, 2013

(87) PCT Pub. No.: WO2012/055933
PCT Pub. Date: May 3, 2012

(65) Prior Publication Data
US 2013/0224287 A1    Aug. 29, 2013

(30) Foreign Application Priority Data

Oct. 26, 2010  (EP) .................... 10188832

(51) Int. Cl.
| | |
|---|---|
| A61K 39/395 | (2006.01) |
| A61K 9/127 | (2006.01) |
| A61K 9/00 | (2006.01) |
| A61K 39/00 | (2006.01) |
| A61K 39/385 | (2006.01) |
| A61K 39/39 | (2006.01) |
| A61K 47/48 | (2006.01) |
| C07K 16/18 | (2006.01) |
| G01N 33/68 | (2006.01) |

(52) U.S. Cl.
CPC .......... *A61K 9/1278* (2013.01); *A61K 9/0019* (2013.01); *A61K 9/127* (2013.01); *A61K 9/1271* (2013.01); *A61K 39/0007* (2013.01); *A61K 39/385* (2013.01); *A61K 39/39* (2013.01); *A61K 47/48038* (2013.01); *A61K 47/48238* (2013.01); *A61K 47/48815* (2013.01); *C07K 16/18* (2013.01); *G01N 33/6896* (2013.01); *A61K 2039/55555* (2013.01); *A61K 2039/55561* (2013.01); *A61K 2039/55572* (2013.01)

(58) Field of Classification Search
None
See application file for complete search history.

(56) References Cited

U.S. PATENT DOCUMENTS

| | | |
|---|---|---|
| 4,565,696 A | 1/1986 | Heath et al. |
| 5,540,935 A | 7/1996 | Miyazaki et al. |
| 5,672,662 A | 9/1997 | Harris et al. |
| 5,721,106 A | 2/1998 | Maggio et al. |
| 5,885,613 A | 3/1999 | Holland et al. |
| 6,169,166 B1 | 1/2001 | Brun et al. |
| 6,521,211 B1 | 2/2003 | Unger et al. |
| 6,521,635 B1 | 2/2003 | Bates et al. |
| 7,378,469 B2 | 5/2008 | Kozlowski |
| 2002/0025312 A1 | 2/2002 | Tagawa et al. |
| 2003/0108551 A1 | 6/2003 | Nicolau et al. |
| 2004/0180002 A1 | 9/2004 | Young et al. |
| 2004/0242845 A1 | 12/2004 | Nicolau et al. |
| 2004/0248799 A1 | 12/2004 | Holaday et al. |
| 2007/0032408 A1 | 2/2007 | Holmes et al. |
| 2008/0233181 A1 | 9/2008 | Nagy et al. |

FOREIGN PATENT DOCUMENTS

| | | |
|---|---|---|
| AU | 2004/262472 A1 | 2/2005 |
| EP | 0203676 A2 | 12/1986 |
| EP | 1 270 592 B1 | 9/2004 |
| JP | 7-291853 | 11/1995 |
| JP | 8-501925 | 3/1996 |
| JP | 11-152234 | 6/1998 |
| JP | 2002-500165 A1 | 7/1999 |
| JP | 2003-518151 | 6/2001 |
| JP | 2002-047298 A | 2/2002 |
| JP | 2007-527870 A | 10/2007 |
| WO | WO 93/25700 A1 | 12/1993 |
| WO | WO 94/10198 A1 | 5/1994 |
| WO | WO 96/25435 A1 | 8/1996 |
| WO | WO 98/46636 A2 | 10/1998 |
| WO | WO 99/27944 A1 | 6/1999 |
| WO | WO 99/41279 A2 | 8/1999 |
| WO | WO 99/42130 A1 | 8/1999 |
| WO | WO 00/72876 A2 | 12/2000 |

(Continued)

OTHER PUBLICATIONS

International Search Report and Written Opinion dated Mar. 16, 2012 for PCT/EP2011/068797, pp. 1-11.
International Preliminary Report on Patentability for PCT/EP2011/068797 dated May 10, 2013, pp. 1-9.
International Preliminary Report on Patentability for PCT/EP2011/063933 dated Feb. 12, 2013, pp. 1-7.
International Search Report and Written Opinion dated Nov. 29, 2011 in PCT International Patent Application No. PCT/EP2011/063933, pp. 1-3.

(Continued)

*Primary Examiner* — Yunsoo Kim
(74) *Attorney, Agent, or Firm* — F. Brent Nix, Esq.; Johnson, Marcou & Isaacs, LLC

(57) ABSTRACT

The present invention relates to method for preparing liposome-based constructs comprising a peptide, particularly an antigenic peptide, of interest modified through hydrophobic moieties reconstituted in liposomes and to the antigenic constructs obtained with said method. The invention further relates to the use of said constructs for the therapeutic and diagnostic use in the treatment of diseases and disorders, which are caused by or associated with proteopathy such as Alzheimer's Disease.

3 Claims, 9 Drawing Sheets

(56) References Cited

FOREIGN PATENT DOCUMENTS

| | | |
|---|---|---|
| WO | WO 00/72880 A2 | 12/2000 |
| WO | WO 01/18169 A2 | 3/2001 |
| WO | WO 01/62284 A2 | 8/2001 |
| WO | WO 02/09748 A1 | 2/2002 |
| WO | WO 02/21141 A2 | 3/2002 |
| WO | WO 02/074243 A3 | 9/2002 |
| WO | WO 03/000719 A2 | 1/2003 |
| WO | WO 03/015812 A2 | 2/2003 |
| WO | WO 03/039467 A2 | 5/2003 |
| WO | WO 2004/013172 A2 | 2/2004 |
| WO | WO 2004/069182 A2 | 8/2004 |
| WO | WO 2005/081872 A2 | 9/2005 |
| WO | WO 2006/066003 A2 | 6/2006 |
| WO | WO 2007/068411 A2 | 6/2007 |
| WO | WO 2007/068412 A2 | 6/2007 |
| WO | WO 2010/115843 A2 | 10/2010 |

OTHER PUBLICATIONS

Allen, T. et al., "Use of the Post-Insertion Method for the Formation of Ligand-Coupled Liposomes," Cellular & Molecular Biology Letters, 2002, vol. 7, pp. 889-894.

Allison, A. et al., "Liposomes as Immunological Adjuvants," Nature Nov. 15, 1974, vol. 252, p. 252.

Alving, C. et al., "Liposomes as Carriers of Peptide Antigens: Induction of Antibodies and Cytoxic T Lymphocytes to Conjugated and Unconjugated Peptides," Immunological Reviews 1995, No. 145, pp. 1-27.

Fieser, T. et al., "Influence of Protein Flexibility and Peptide Conformation on Reactivity of Monoclonal Anti-Peptide Antibodies with a Protein α-Helix," Proc. Natl. Acad. Sci., Dec. 1987, vol. 84, pp. 8568-8572.

Frisch, B. et al., "Parameters Affecting the Immunogenicity of a Liposome-Associated Synthetic Hexapeptide Antigen," Eur. J. Immunol. 1991, vol. 21, pp. 185-193.

Frisch B. et al., "Synthetic Peptide-Based Highly Immunogenic Liposomal Constructs," Methods in Enzymology, Jan. 1, 2003, vol. 373, pp. 51-73.

Guan, H. et al., "Liposomal Formulations of Synthetic MUC1 Pepdtides: Effects of Encapsulation versus Surface Display of Peptides on Immune Responses," Bioconjugate Chemistry 1998, vol. 9, No. 4, pp. 451-458.

Kersten, G. et al., "Liposomes and ISCOMS as Vaccine Formulations," Biochimica et Biophysica Acta 1241 1995, pp. 117-138.

Lu, Stephen M. et al., "A de Novo Designed Template for Generating Conformation-Specific Antibodies That Recognize α-Helices in Proteins," The Journal of Biological Chemistry, Jun. 28, 2002, vol. 277, No. 26, pp. 23515-23524.

Moreira, J. et al., "Use of the Post-Insertion Technique to Insert Peptide Ligands into Pre-Formed Stealth Liposomes with Retention of Binding Activity and Cytotoxicity," Pharmaceutical Research, Mar. 2002, vol. 19, No. 3, pp. 265-269.

Muhs, A. et al., "Liposomal Vaccines with Conformation-Specific Amyloid Peptide Antigens Define Immune Response and Efficacy in APP Transgenic Mice," PNAS, Jun. 5, 2007, vol. 104, No. 23, pp. 9810-9815.

Nicolau, C. et al., "A Liposome-Based Therapeutic Vaccine Aginst β-Amyloid Plaques on the Pancreas of Transgenic NORBA Mice," PNAS, Feb. 19, 2002, vol. 99, No. 4, pp. 2332-2337.

O'Nuallain, B. et al., "Conformational Abs Recognizing a Generic Amyloid Fibril Epitope," PNAS, Feb. 5, 2002, vol. 99. No. 3, pp. 1485-1490.

Schmechel, A. et al., "Alzheimer β-Amyloid Homodimers Facilitate Aβ Fibrillization and the Generation of Conformational Antibodies," The Journal of Biological Chemistry, Sep. 12, 2003, vol. 278, No. 37, pp. 35317-35324.

Torchilin, V., "Recent Advances with Liposomes as Pharmaceutical Carriers," Nature Reviews, Feb. 2005, vol. 4, pp. 145-160.

Japanese Office Action dated Aug. 3, 2015 for counterpart Japanese Patent Application No. 2013-535421, English translation included, pp. 1-8.

Chinese Office Action dated Jul. 30, 2014 in counterpart Chinese application No. 201180051932.3.

Huang et al., "Characterization of Antibody Covalently Coupled to Liposomes," Biochimica et Biophysica Acta, Dec. 31, 1982, vol. 716, pp. 140-150.

JP Office Action issued in Appl. No. 2006-554250, pp. 1-4, Dec. 15, 2010.

Japanese Office Action issued in JP Application No. 2006-554250, JP Office Action, pp. 1-10, Sep. 21, 2011.

Amyloid, Wikipedia—http://en.wikipedia.org/wiki/Amyloid, pp. 1-6, Sep. 21, 2009.

Definition of Amyloid, MedicineNet.com, pp. 1, Aug. 4, 2009.

Pegasys as Treatment for People with Hepatitis B, Website—Medical Brochure information, pp. 1-2, May 16, 2007.

Japanese Office Action—Application No. 2011-131772 (with English translation), pp. 1-6, Feb. 21, 2013.

Chinese Office Action—Application No. 2005-800125877, pp. 1-2, Jan. 20, 2012.

Sigma-Aldrich—FLUKA AG—Cat. No. 79898—O-[2-(boc-amino)-ethyl]-O'-[2-(diglycolyl-amino)ethyl]decaehtylene glycol, FLUKA AG, pp. 1, Jan. 1, 2002.

Abuchowski, Alteration of Immunological Properties of Bovine Serum Albumin by Covalent Attachment of Polyethylene Glycol, The Journal of Biological Chemistry, vol./Iss: 252 (11), pp. 3578-3581, Jan. 1, 1977.

Abuchowski et al., Effect of Attachment of Polyethylene Glycol on Immunogenicity and Circulating Life of Bovine Liver Catalase, The Journal of Biological Chemistry vol./Iss: 252 (11), pp. 3582-3586, Jan. 1, 1977.

Allen et al., Liposomes Containing Synthetic Lipid Derivatives of Poly(ehtylene glycol) Show Prolonged Circulation Half-lives in Vivo (Applicants only have Abstract), Biochim Biophys Acta, vol./Iss: 1066 (1), pp. 29-36, Jul. 1, 1991.

Barret et al., Evaluation of Quinacrine Treatment for Prion Diseases, Journal of Virology, vol./Iss: 77 (13), pp. 8462-8469, Jan. 1, 2003.

Bashir et al., Generation of a Monoclonal Antibody to P-Glycoprotein Peptides using Tuberculin-PPD as a Carrier, Virchows Arch., vol./Iss: 432, pp. 279-287, Jan. 1, 1998.

Candido et al., Local Administration of Dendritic Cells Inhibits Established Breast Tumor Growth: Implications for Apoptosis-Inducing Agents, Cancer Research, vol./Iss: 61, pp. 228-236, Jan. 1, 2001.

Chen et al., Internal Duplication and Homology with Bacterial Transport Proteins in the mdr1 (P-Glycoprotein) Gene from Multidrug-Resistant Human Cells, Cell, vol./Iss: 47, pp. 381-389, Jan. 1, 1986.

De Gioia et al., Conformational Polymorphism of the Amyloidogenic and Neurotoxic Peptide Homologous to Residues 106-126 of the Prior Protein, The Journal of Biological Chemistry, vol./Iss: 269 (11), pp. 7859-7862, Mar. 18, 1994.

Deprez et al., Comparative Efficiency of Simple Lipoprotein Constructs for in vivo Induction of Virus-Specific CTL, Vaccine, vol./Iss: 14 (5), pp. 375-382, Jan. 1, 1998.

Endicott et al., The Biochemistry of P-Glycoprotein-Mediated Multidrug Resistance, Annual Reviews Biochemistry, vol./Iss: 58, pp. 137-171, Jan. 1, 1989.

Felix, Arthur, Site-Specific Poly (ethylene glycol)ylation of Peptides, American Chemical Society—ACS Symposium Seminar, vol./Iss: 680, pp. 218-238, Jan. 1, 1997.

Fleiner et al., Studies on Protein-Liposome Coupling Using Novel Thiol-Reactive Coupling Lipids: Influence of Spacer Length and Polarity, Bioconjugate Chemistry, vol./Iss: 12, pp. 470-475, Jan. 1, 2001.

Fries et al., Liposomal Malaria Vaccine in Humans: A Safe and Potent Adjuvant Strategy, Proceedings of the National Academy of Science USA, vol./Iss: 89, pp. 358-362, Jan. 1, 1992.

Frisch et al., Synthesis of Short Polyoxyethylene-Based Herobifunctional Cross-Linking Reagents. Application to the Coupling of Peptides in Liposomes, Bioconjugate Chemistry, vol./Iss: 7 (2), pp. 180-186, Jan. 1, 1996.

(56) References Cited

OTHER PUBLICATIONS

Fukuda et al., Synthesis, Aggregation, and Neurotoxicity of the Alzheimer's Aβ1-42 Amyloid Peptide and Its Isoaspartyl Isomers, *Bioorganic and Medicinal Chemistry*, vol./Iss: 9, pp. 953-956, Jan. 1, 1999.
Gaertner et al., Site-Specific Attachment of Functionalized Poly-(ethylene glycol) to the Amino Terminus of Proteins, *Bioconjugate Chemistry*, vol./Iss: 7, pp. 38-44, Jan. 1, 1996.
Gatouillat et al., Immunization with Liposome-Anchored Pegylated Peptides Modulates Doxorubicin Sensitivity in P-Glycoprotein-Expressing P388 Cells, *Science Direct—Cancer Letters*, vol./Iss: 257, pp. 165-171, Jan. 1, 2007.
Goldsby et al., Immunology—Chapter 19 Vaccines, *Immunology—Fourth Edition*, pp. 449-465, Jan. 1, 2002.
Grace et al., Site of Pegylation and Polyethylene Glycol Molecule Size Attenuate Interferon-a Antiviral and Antiproliferative Activities through the JAK/STAT Signaling Pathway, *The Journal of Biological Chemistry*, vol./Iss: 280 (8), pp. 6327-6337, Jan. 1, 2005.
Gura, Systems for Identifying New Drugs Often Faulty, *Science*, vol./Iss: 278, pp. 1041-1042, Nov. 7, 1997.
Janssen et al., Peptide-targeted PEG-liposomes in Anti-angiogenic Therapy, *International Journal of Pharmaceutics*, pp. 55-58, Jan. 1, 2003.
Juliano et al., A Surface Glycoprotein Modulating Drug Permeability in Chinese Hamster Ovary Cell Mutants, *Biochmica et Biophysica Acta*, vol./Iss: 455, pp. 152-162, Jan. 1, 1976.
Kaiser, J., First Pass at Cancer Genome Reveals Complex Landscape, *Science*, vol./Iss: 313, pp. 1370, Sep. 8, 2006.
Kim, Y., Office Action issued in copending U.S. Appl. No. 10/958,211, filed Oct. 4, 2004, pp. 1-8, Dec. 18, 2009.
Kim, Y., Office Action issued in copending U.S. Appl. No. 10/958,211, filed Oct. 4, 2004, pp. 1-6, Nov. 29, 2007.
Kim, Y., Office Action issued in copending U.S. Appl. No. 10/958,211, filed Oct. 4, 2004, pp. 1-8, Oct. 29, 2010.
Kim, Y., Office Action issued in copending U.S. Appl. No. 10/958,211, filed Oct. 4, 2004, pp. 1-12, Sep. 8, 2008.
Kim, Y., Office Action issued in copending U.S. Appl. No. 10/958,211, filed Oct. 4, 2004, pp. 1-8, Jul. 16, 2010.
Kim, Y., Office Action issued in copending U.S. Appl. No. 10/958,211, filed Oct. 4, 2004, pp. 1-12, Jun. 4, 2007.
Kim, Y., Office Action issued in copending U.S. Appl. No. 10/958,211, filed Oct. 4, 2004 , pp. 1-12, May 8, 2009.
Kim, Y., International Search Report and Written Opinion—Appl. No. PCT/US05/05285, pp. 1-16, May 2, 2007.
Kim, Y., Office Action issued in copending U.S. Appl. No. 10/958,211, filed Oct. 4, 2004, pp. 1-10, Apr. 13, 2011.
Office Action issued in U.S. Appl. No. 10/958,211, USPTO Office Action, pp. 1-11, Jul. 16, 2010.
Klohs et al., Resistance to Anthrapyrazoles and Anthracyclines in Multidrug-Resistant P388 Murine Leukemia Cells: Reversal by Calcium Blockers and Calmodulin Antagonists, *Cancer Research*, vol./Iss: 46, pp. 4352-4356, Sep. 1, 1986.
Kodera et al., "Proteins, Nucleic Acids and Enzymes"—Article cited in JP Office Action of Appl. No. 2006-554250, *Tanpakushitsu Kakusan Koso (PNAS)*, vol./Iss: 48 (11), pp. 1527-1533, Aug. 10, 2003.
Kodera et al., Proteins, Nucleic Acids and Enzymes (English abstract), vol./Iss: 48 (11), pp. 1527-1533, Jan. 1, 2003.
Marincola et al., Tumors as Elusive Targets of T-Cell-Based Active Immunotherapy, *Trends in Immunology* vol./Iss: 24 (6), pp. 334-341, Jun. 1, 2003.
Mechetner et al., Efficient Inhibition of P-Glycoportein-Mediated Multidrug Resistance with a Monoclonal Antibody, *Proceedings of the National Academy Science USA*, vol./Iss: 89, pp. 5824-5828, Jul. 1, 1992.
Miller et al., P-Glycoprotein Expression in Malignant Lymphoma and Reversal of Clinical Drug Resistance with Chemotherapy Plus High0Dose Verapamil, *Journal of Clinical Oncology*, vol./Iss: 9 (1), pp. 17-24, Jan. 1, 1991.
Muhs et al., Improved Memory Capacity of Amyloid Precursor Protein Transgenic mice Through Passive Administration of a Monoclonal Antibody Inducing a Conformational Shift of Amyloid-Beta, *The Journal of the Alzheimer's Association*, vol./Iss: 2 (3), pp. S21, Jan. 17, 2006.
Pawlak-Robin et al., Inhibition of Multidrug Resistance by Immunisation with Synthetic P-glycoprotein-derived Peptides, *European Journal of Cancer*, vol./Iss: 40, pp. 606-613, Jan. 1, 2004.
Petkova et al., A Structural Model for Alzheimer's β-Amyloid Fibrils Based on Experiemental Constraints from Solid State NMR, *Proceedings of the National Academy of Science USA*, vol./Iss: 99 (26), pp. 16742-16747, Dec. 24, 2002.
Pierre et al., In vitro and In vivo Circumvention of Multidrug Resistence by Servier 9788, a Novel Triazinoaminopiperidine Derivative, *Investigational New Drugs*, vol./Iss: 10, pp. 137-148, Jan. 1, 1992.
Roberts et al., Chemistry for Peptide and Protein PEGylation, *Advanced Delivery Reviews*, vol./Iss: 54, pp. 459-476, Jan. 1, 2002.
Schinkel et al., Binding Properties of Monoclonal Antibodies Recognizing External Epitopes of the Human MDR1 P-Glycoprotein, *Int. Journal of Cancer*, vol./Iss: 55, pp. 478-484, Jan. 1, 1993.
Schnolzer et al., Constructing Proteins by Dovetailing Unprotected Synthetic Peptides: Backbone-Engineered HIV Protease, *Science*, vol./Iss: 256 (5054), pp. 221-225, Apr. 10, 1992.
Solomon, B., Immunological Approach for the Treatment of Alzheimer's Disease, *Journal of Molecular Neuroscience*, vol./Iss: 20, pp. 283-286, Jan. 1, 2003.
Stober et al., Synthesis of Characteristic Lipopeptides of the Human N-Ras Protein and their Evaluation as Possible Inhibitors of Protein Farnesyl Transferase, *Bioorganic & Medicinal Chemistry*, vol./Iss: 5 (1), pp. 75-83, Jan. 1, 1997.
Stupp et al., Ventricular Arrhythmia and Torsade de Pointe: Dose Limiting Toxicities of the MDR-Modulator S9788 in a Phase I Trials, *Annals of Oncology*, vol./Iss: 9, pp. 1233-1242, Jan. 1, 1998.
Thiebault et al., Cellular Localization of the Multidrug-Resistance Gene Product P-Glycoprotein in Normal Human Tissues, *Proceedings of the National Academy of Science USA*, vol./Iss: 84, pp. 7735-7738, Nov. 1, 1987.
Torchilin, V., Recent Advances with Liposomes as Pharmaceutical Carriers, *Nature Reviews*, vol./Iss: 4, pp. 145-160, Feb. 1, 2005.
Tosi et al., Immune Response Against the Murine MDRI Protein Induced by Vaccination with Synthetic Lipopeptides in Liposomes, *Biochemical and Biophysical Research Communications*, vol./Iss: 212 (2), pp. 494-500, Jul. 17, 1995.
Tsuruo, T., Circumvention of Drug Resistance with Calcium Channel Blockers and Monoclonal Antibodies, *Drug Resistance in Cancer Therapy*, pp. 73-95, Jan. 1, 1989.
Van Der Bliek et al., Sequence of mdr3 cDNA Encoding a Human P-Glycoprotein, *Gene*, vol./Iss: 71, pp. 401-411, Jan. 1, 1988.
Wiame, Ilse, EPO Search Report issued in Appl. No. EP 12 15 3152, pp. 1-10, May 9, 2012.
Wolf-Klein et al., Conceptualizing Alzheimer's Disease as a Terminal Medical Illness (Abstract only), *American Journal of Hospital Palliative Care*, vol./Iss: 24 (1), pp. 77-82, Feb. 1, 2007.
Yang et al., Treatment of Multidrug Resistant (MDR1) Murine Leukemia with P-Glycoprotein Substrates Accelerates the Course of the Disease, *Biochemical and Biophysical Research*, vol./Iss: 266, pp. 167-163, Jan. 1, 1999.
Zhang et al., Mutliple-Peptide Conjugates for Binding β-Amyloid Plaques of Alzheimer's Disease, *Bioconjugate Chemistry*, vol./Iss: 14, pp. 86-92, Dec. 7, 2002.
Ishida, et al., "A Combinatorial Approach to Producing Sterically Stabilized (Stealth) Immunoliposomal Drugs", FEBS Letters, vol. 460, 1999, 129-133.

SEQUENCE LISTING

```
<160> NUMBER OF SEQ ID NOS: 12

<210> SEQ ID NO 1
<211> LENGTH: 30
<212> TYPE: PRT
<213> ORGANISM: Homo sapiens
<220> FEATURE:
<221> NAME/KEY: VARIANT
<222> LOCATION: (18)..(18)
<223> OTHER INFORMATION: /replace="phosphorylated Serine"
<220> FEATURE:
<221> NAME/KEY: VARIANT
<222> LOCATION: (26)..(26)
<223> OTHER INFORMATION: /replace="phosphorylated Serine"

<400> SEQUENCE: 1

Arg Glu Asn Ala Lys Ala Lys Thr Asp His Gly Ala Glu Ile Val Tyr
1               5                   10                  15

Lys Ser Pro Val Val Ser Gly Asp Thr Ser Pro Arg His Leu
            20                  25                  30

<210> SEQ ID NO 2
<211> LENGTH: 16
<212> TYPE: PRT
<213> ORGANISM: Homo sapiens
<220> FEATURE:
<221> NAME/KEY: VARIANT
<222> LOCATION: (14)..(14)
<223> OTHER INFORMATION: /replace="phosphorylated Tyrosin"

<400> SEQUENCE: 2

Arg Gln Glu Phe Glu Val Met Glu Asp His Ala Gly Thr Tyr Gly Leu
1               5                   10                  15

<210> SEQ ID NO 3
<211> LENGTH: 16
<212> TYPE: PRT
<213> ORGANISM: Homo sapiens
<220> FEATURE:
<221> NAME/KEY: VARIANT
<222> LOCATION: (7)..(7)
<223> OTHER INFORMATION: /replace="phosphorylated Threonine"
<220> FEATURE:
<221> NAME/KEY: VARIANT
<222> LOCATION: (9)..(9)
<223> OTHER INFORMATION: /replace="phosphorylated Serine"
```

```
<400> SEQUENCE: 3

Pro Gly Ser Arg Ser Arg Thr Pro Ser Leu Pro Thr Pro Pro Thr Arg
1               5                   10                  15

<210> SEQ ID NO 4
<211> LENGTH: 16
<212> TYPE: PRT
<213> ORGANISM: Homo sapiens
<220> FEATURE:
<221> NAME/KEY: VARIANT
<222> LOCATION: (7)..(7)
<223> OTHER INFORMATION: /replace="phosphorylated Serine"
<220> FEATURE:
<221> NAME/KEY: VARIANT
<222> LOCATION: (10)..(10)
<223> OTHER INFORMATION: /replace="phosphorylated Threonine"

<400> SEQUENCE: 4

Gly Tyr Ser Ser Pro Gly Ser Pro Gly Thr Pro Gly Ser Arg Ser Arg
1               5                   10                  15

<210> SEQ ID NO 5
<211> LENGTH: 16
<212> TYPE: PRT
<213> ORGANISM: Homo sapiens
<220> FEATURE:
<221> NAME/KEY: VARIANT
<222> LOCATION: (4)..(4)
<223> OTHER INFORMATION: /replace="phosphorylated Serine"
<220> FEATURE:
<221> NAME/KEY: VARIANT
<222> LOCATION: (12)..(12)
<223> OTHER INFORMATION: /replace="phosphorylated Serine"

<400> SEQUENCE: 5

Val Tyr Lys Ser Pro Val Val Ser Gly Asp Thr Ser Pro Arg His Leu
1               5                   10                  15

<210> SEQ ID NO 6
<211> LENGTH: 18
<212> TYPE: PRT
<213> ORGANISM: Homo sapiens
<220> FEATURE:
<221> NAME/KEY: VARIANT
<222> LOCATION: (4)..(4)
<223> OTHER INFORMATION: /replace="phosphorylated Serine"
<220> FEATURE:
<221> NAME/KEY: VARIANT
<222> LOCATION: (9)..(9)
<223> OTHER INFORMATION: /replace="phosphorylated Serine"

<400> SEQUENCE: 6

Gly Asp Thr Ser Pro Arg His Leu Ser Asn Val Ser Ser Thr Gly Ser
1               5                   10                  15

Ile Asp

<210> SEQ ID NO 7
<211> LENGTH: 17
<212> TYPE: PRT
<213> ORGANISM: Homo sapiens
<220> FEATURE:
<221> NAME/KEY: VARIANT
<222> LOCATION: (3)..(3)
<223> OTHER INFORMATION: /replace="phosphorylated Serine"
<220> FEATURE:
<221> NAME/KEY: VARIANT
<222> LOCATION: (6)..(6)
<223> OTHER INFORMATION: /replace="phosphorylated Threonine"
<220> FEATURE:
<221> NAME/KEY: VARIANT
```

```
<222> LOCATION: (13)..(13)
<223> OTHER INFORMATION: /replace="phosphorylated Threonine"
<220> FEATURE:
<221> NAME/KEY: VARIANT
<222> LOCATION: (15)..(15)
<223> OTHER INFORMATION: /replace="phosphorylated Serine"

<400> SEQUENCE: 7

Pro Gly Ser Pro Gly Thr Pro Gly Ser Arg Ser Arg Thr Pro Ser Leu
1               5                   10                  15

Pro

<210> SEQ ID NO 8
<211> LENGTH: 12
<212> TYPE: PRT
<213> ORGANISM: Homo sapiens
<220> FEATURE:
<221> NAME/KEY: VARIANT
<222> LOCATION: (3)..(3)
<223> OTHER INFORMATION: /replace="phosphorylated Serine"

<400> SEQUENCE: 8

His Leu Ser Asn Val Ser Ser Thr Gly Ser Ile Asp
1               5                   10

<210> SEQ ID NO 9
<211> LENGTH: 10
<212> TYPE: PRT
<213> ORGANISM: Homo sapiens
<220> FEATURE:
<221> NAME/KEY: VARIANT
<222> LOCATION: (6)..(6)
<223> OTHER INFORMATION: /replace="phosphorylated Serine"

<400> SEQUENCE: 9

Val Ser Gly Asp Thr Ser Pro Arg His Leu
1               5                   10

<210> SEQ ID NO 10
<211> LENGTH: 15
<212> TYPE: PRT
<213> ORGANISM: Homo sapiens

<400> SEQUENCE: 10

Asp Ala Glu Phe Arg His Asp Ser Gly Tyr Glu Val His His Gln
1               5                   10                  15

<210> SEQ ID NO 11
<211> LENGTH: 19
<212> TYPE: PRT
<213> ORGANISM: Homo sapiens
<220> FEATURE:
<221> NAME/KEY: VARIANT
<222> LOCATION: (1)..(1)
<223> OTHER INFORMATION: /replace="acetylated Lysine"
<220> FEATURE:
<221> NAME/KEY: VARIANT
<222> LOCATION: (2)..(2)
<223> OTHER INFORMATION: /replace="acetylated Lysine"
<220> FEATURE:
<221> NAME/KEY: VARIANT
<222> LOCATION: (18)..(18)
<223> OTHER INFORMATION: /replace="acetylated Lysine"
<220> FEATURE:
<221> NAME/KEY: VARIANT
<222> LOCATION: (19)..(19)
<223> OTHER INFORMATION: /replace="acetylated Lysine"

<400> SEQUENCE: 11
```

-continued

```
Lys Lys Asp Ala Glu Phe Arg His Asp Ser Gly Tyr Glu Val His
1               5                   10                  15

His Gln Lys Lys

<210> SEQ ID NO 12
<211> LENGTH: 19
<212> TYPE: PRT
<213> ORGANISM: Homo sapiens
<220> FEATURE:
<221> NAME/KEY: VARIANT
<222> LOCATION: (1)..(1)
<223> OTHER INFORMATION: /replace="palmitoylated Lysine"
<220> FEATURE:
<221> NAME/KEY: VARIANT
<222> LOCATION: (2)..(2)
<223> OTHER INFORMATION: /replace="palmitoylated Lysine"
<220> FEATURE:
<221> NAME/KEY: VARIANT
<222> LOCATION: (18)..(18)
<223> OTHER INFORMATION: /replace="palmitoylated Lysine"
<220> FEATURE:
<221> NAME/KEY: VARIANT
<222> LOCATION: (19)..(19)
<223> OTHER INFORMATION: /replace="palmitoylated Lysine"

<400> SEQUENCE: 12

Lys Lys Asp Ala Glu Phe Arg His Asp Ser Gly Tyr Glu Val His
1               5                   10                  15

His Gln Lys Lys
```

METHOD FOR PREPARING LIPOSOME-BASED CONSTRUCTS

CROSS REFERENCE TO RELATED APPLICATIONS

This application is a 35 U.S.C. §371 national phase patent application of International Patent Application Number PCT/EP2011/068797, filed on Oct. 26, 2011 and claims the benefit of European Patent Application Number 10188832.9, filed Oct. 26, 2010.

The present invention relates to an improved method for preparing liposome-based constructs comprising a peptide of interest, particularly an antigenic peptide of interest, modified through hydrophobic moieties reconstituted in liposomes and to the antigenic constructs obtained with said method. The invention further relates to the use of said constructs for therapeutic and diagnostic purposes, particularly to the use in the treatment of diseases and disorders caused by or associated with proteopathy such as Alzheimer's Disease.

Liposomes have moved a long way from being just another exotic object of biophysical research to become a pharmaceutical carrier of choice for numerous practical applications (Torchilin, Nature Reviews, 2005, 4, 145-160). The liposomes are artificial vesicles, mostly made of (phospho)lipids and may contain drugs or soluble antigens in their internal, aqueous volume or amphipathic antigens, such as membrane proteins, incorporated in the bilayer. Antigens from many microorganisms and tumor cells have been incorporated into such liposomes with a detailed characterization and in vivo testing. Clinical studies with antigen containing liposomes have indicated that they are safe and generally induce no severe adverse effects (Kersten and Crommelin, Biochimica et Biophysica Acta 1995, 1241, 117-138).

The idea to use liposomes as vehicles for the presentation of antigens was tested more than 30 years ago (Allison and Gregoriadis, Nature, 1974, 252, 252) For example, it was shown that diphtheria toxoid incorporated in liposomes is more immunogenic than its free form. Antigens presented via liposomes can induce humoral as well as cellular immune responses. Most of the liposomal vaccines developed so far have been prepared by antigen entrapment within the aqueous lumen of liposomes. In addition, there are recent reports in the literature on the use of liposomes which carry hydrophobic or amphiphilic antigens randomly distributed on their surface (i.e. antigens aleatorily facing either the internal or external aqueous solution) (Muhs et al., PNAS, 2007, 104, 9810-9810; Nicolau et al., PNAS, 2002, 99, 2332-2337; WO2007/068411). Frisch et al. have observed that, in contrast to encapsulated peptides, the expression of small B cell epitopes at the surface of vesicles containing monophosphoryl lipid A (MPLA) as adjuvant was able to induce strong and specific humoral responses (production of antibodies) (Frisch, Eur J Immunol 1991; 21:185; Alving et al., Immunol Rev 1995; 145:5). Therefore, antigens presented on the surface of liposomes are probably more indicated for therapeutic vaccines, where a non-inflammatory response is desired. Hence, the addition of antigens after liposome formation followed by its integration in the liposomes should provide single distribution of antigen in the external liposome lipid layer. Actually, post-insertion methods have been developed and are widely reported in the literature, which can be resumed as coupling between the antigen and a reactant on the external lipid surface of liposomes, or the use of pegylated peptides (Allen et al., Cellular & Molecular Biology Letters, 2002, 7, 217-219; Guan et al., Bioconjugate Chem, 1998, 9, 451-458; Moreira et al., Pharmaceutical Research, 2002, 19, 265-269) However, a main limitation of post-insertion methods using chemical conjugation (e.g. stable thioether bonds or bioreducible disulfide linkages) described in the art is the lack of regiospecificity, need for insertion of reaction groups in the liposomes and additional down-stream processes. The so-produced liposome-based constructs are not capable of sterile filtration. Further, covalent conjugation of peptides to the external liposome layer is not yet applicable for different kind of antigens such as hydrophobic peptides.

One commonly used method relates to the use of pegylated peptides which is based on the formation of micelles by peptide-PEG-phospholipid conjugates (sometimes with the aid of additional surfactants). Upon incubation with pre-formed liposomes, this method leads under optimized conditions to a spontaneous transfer (molecular translocation) of the peptide conjugate into the outer membrane leaflet of the liposome. However, this method is susceptible to vesicle destabilization (in case additional surfactants are needed) and can induce side immune responses (as PEG can be immunogenic).

There is therefore an unmet need for a method providing a liposome-based construct, wherein the method allows to overcome most or all of the disadvantages of the prior art methods and provides improved antigenic constructs which exhibit desirable properties in terms of:
yield,
vesicle stability,
homogeneity,
region specificity (topology, outer and inner distribution of peptides),
filterability,
presentation of the majority of the antigen on the liposomal surface, etc.

This unmet need is addressed and solved by the present invention by providing methods and constructs as defined by the features of independent claims. Preferred embodiments are subject of the dependent claims.

The method according to the invention now makes it possible to post-insert different peptide (e.g. antigen) types and/or adjuvant types to the external layer of preformed liposomes in different concentrations. The method according to the invention comprises pre-forming of liposomes in solution and modification of peptides, particularly of antigenic peptides, through hydrophobic moieties such that the modified peptide is available in a micellar form. The method further comprises releasing of the peptides from the micelles by inducing micellar breakdown followed by integration into the pre-formed liposome. This integration process is driven by hydrophobic interactions of the modified peptide, the antigen and/or the adjuvant with the (phospho)lipid bilayer of the liposomes. In particular, the solubilizing of the modified peptide, particularly of the modified antigenic peptide and/or adjuvant, into the external layer of liposomes is accomplished without the aid of any chemical reaction or additional molecule modification, by diluting the solubilized peptide, particularly the solubilized antigenic peptide or adjuvant (initially presented in micellar form), below the critical micellar concentration of the surfactant. The free form of the peptide, particularly the free form of the antigenic peptide and/or adjuvant, is then integrated in the external layer of the liposomes due to the solubilization of their hydrophobic domains in the acyl moiety of the phospholipids. Thus, the method according to the invention provides for a stock of "empty liposomes" being disposable for loading according to the respective needs.

Advantageously, the method and constructs disclosed and claimed herein lead to high yields of peptide and/or adjuvant incorporation with a unique molecular display on the liposome facing the external layer of the liposome bilayer. The method of the invention further results in liposome preparations which show a homogenous size distribution with a polydispersity index in the range of between 0.2 and 0.6, particularly of 0.22 to 0.35, particularly of 0.25. Further, the method and constructs allow for a high bioavailability of peptide and/or adjuvant for the immune system and, as a consequence, an improved immune response. Within the method according to the invention, no adjuvant degradation, e.g. MPLA degradation, occurs and, thus, an increased batch reproducibility is provided. The constructs prepared by the method of the invention are stable, capable of sterile filtration (particle size<200 nm) and do not induce side immune responses.

In particular, the constructs prepared by the method of the invention can be stored at a temperature of between 0° C. and 10° C., particularly of between 2° C. and 6° C., but especially at 5° C. and remain stable for a time period of between 1 month and 6 month or more, particularly of between 2 month and 4 month, but especially for 3 month.

Further, the method of the invention and as described herein in the various embodiments enables a fast and industrial-scale manufacturing of the constructs with reduced losses of peptide (<25%) and adjuvant (<25%) during the preparation process resulting in decreased cost during manufacturing.

In particular, any losses of peptide and/or adjuvant are less than 30%, particularly less than 25%, but especially less than 20%, or beneath.

In particular, the present invention relates to a method of preparing a liposome-based construct comprising a peptide of interest, particularly an antigenic peptide of interest, according to the invention and as described herein in the various embodiments, wherein said peptide is modified through hydrophobic moieties and is reconstituted in a liposome, comprising the steps of i) preparing liposomes in solution; ii) preparing a modified peptide, particularly a modified antigenic peptide, by adding to the N- and/or C-terminus of the peptide molecule at least one hydrophobic moiety; iii) solubilizing the modified peptide or antigenic peptide in the presence of a surfactant; iv) diluting the solubilized peptide and, optionally, an adjuvant below the critical micellar concentration (CMC) of the surfactant; and v) loading the preformed liposomes with the diluted, solubilized peptide and, optionally, the adjuvant, by adding said peptide and, optionally, said adjuvant, to the preformed liposomal preparation and solubilizing the added peptide and, optionally, the added adjuvant, into the external layer of the liposomes, particularly without the aid of any chemical reaction or additional molecule modification by, for example, coupling a reactant on the external lipid surface of the liposome, or the use of pegylated peptides.

In one embodiment, the invention relates to a method as described herein in the various embodiments, wherein the dilution of the solubilised peptide, particularly the solubilised antigenic peptide, and, optionally, the solubilised adjuvant occurs in the process of adding the peptide and, optionally, the adjuvant to the liposomal solution containing the preformed liposomes.

In one embodiment, the invention relates to a method as described herein in the various embodiments, wherein, the solubilised peptide, particularly the solubilised antigenic peptide, and, optionally, the solubilised adjuvant, containing solution is diluted to reach less than 50%, particularly 40%, 30%, 20%, 15%, 10%, 5%, 4%, 3%, 2%, 1% of the critical micellar concentration (CMC) of the surfactant.

In one embodiment, the present invention relates to a method of preparing a liposome-based construct, particularly a liposome-based antigenic construct, according to the invention and as described herein in the various embodiments, wherein in step v) the preformed liposomes are loaded with one or more different, diluted, solubilized peptides, particularly solubilized antigenic peptides and/or adjuvants as defined herein.

In one embodiment, the present invention relates to a method of preparing a liposome-based construct, particularly a liposome-based antigenic construct according to the invention and as described herein in the various embodiments, wherein the peptide is solubilized before being added to the pre-formed liposomes by adding to the preparation a detergent selected from the group consisting of anionic, cationic, non-ionic and zwitterionic surfactants such as, for example Octyl-Beta-D-Glucopyranoside (B-OG) or Tween-20.

In one embodiment, the invention relates to the method of any one of the preceding embodiments, wherein the pre-formed liposomes are loaded with an adjuvant.

In one embodiment, the adjuvant may be added to the pre-formed liposome after the formation of the liposome, i.e. first the diluted solubilized antigenic peptide is added to the pre-formed liposome preparation followed by the adjuvant, particularly the solubilized adjuvant. Alternatively, first the adjuvant, particularly the solubilized adjuvant, may be added to the pre-formed liposome preparation followed by, or together with, the diluted solubilized antigenic peptide.

The invention thus provides for a method of any one of the preceding embodiments, wherein the adjuvant loading is carried out (a) prior to; (b) together with; or (c) after the loading of the liposomes with the diluted solubilized antigenic peptide.

In one embodiment of the invention, two or more types of liposomes may be combined and used within the method as described herein in the various embodiments. As a non-limiting example, two populations of liposomes may be mixed, i.e. one population comprising liposomes containing an antigenic peptide and another population comprising liposomes solely containing an adjuvant, for the induction of an immune response in a mammal.

In an alternative embodiment, different populations of liposomes may be mixed comprising different antigenic peptides and/or adjuvants. For example, one population of liposomes may comprise liposomes containing on its outer surface a first antigenic peptide such as, for example, a tau protein fragment with or without adjuvant, while a second population of liposomes may comprise liposomes containing a second and different antigenic peptide such as, for example, a beta-amyloid peptide fragment with or without adjuvant. A third population of liposomes may then comprise liposomes solely containing an adjuvant.

In one embodiment, the method comprises a sizing step, particularly a sizing step involving a method selected from the group consisting of homogenisation, extrusion, microfluidics and sonication; or any combination of these methods.

In one embodiment of the invention, the sizing of the liposome particles prepared within the method according to the invention and as described herein in the various embodiments comprises homogenisation and extrusion, which may be either carried out independently of each other or resumed in one step within said sizing method. Moreover, the sizing of the liposome particles may also comprise microfluidics and sonication, which may be used either independently or in combination with another particle sizing method.

The liposomes are of a size smaller than 300 nm, particularly smaller than 250 nm, particularly smaller than 200 nm.

In particular, the liposomes are in a size range of between 20 nm and 300 nm, particularly in a size range of between 40 nm and 250 nm, particularly in a size range of between 50 nm and 200 nm, particularly in a size range of between 100 nm and 200 nm.

In one embodiment, the invention relates to the method of any one of the preceding embodiments, wherein the adjuvant is selected from the group consisting of lipid A, detoxified lipid A, such as monophosphoryl or diphosphoryl lipid A, alum, Pam2CSK4, Pam3CSK4, Pam3CAG, saponins, CpG, lipidated CpG, cationic lipids, lipidated CpG, phosphorothioated PS-CpG-ODNs, CpG oligodeoxynucleotides (CpG-ODN) such as CpG-A, CpG-B or CpG-C. Further adjuvants, that may be used with the method according to the invention are, without intended to be limiting, aluminium phosphate or hydroxide (Al(OH)3, AlPO4), salts of calcium, iron or zirconium, QuilA, QS-21, trehalose dimycolate (TDM), lipoteichoic acid (purified from *Staphylococcus aureus*), DDAB (dimethyldioctadecylammonium (bromide salt)), MF59, L18-MDP & B30-MDP (hydrophobic muramyl-dipeptide derivatives), C12-iE-DAP (diaminopimelic acid)

In one embodiment, the invention relates to the method of any one of the preceding embodiments, wherein at least 70%, 71%, 72%, 73%, 74%, 75%, 76%, 77%, 78%, 79%, 80%, 81%, 82%, 83%, 84%, 85%, 86%, 87%, 89%, 90%, 91%, 92%, 93%, 94%, 95%, 96%, 97%, 98%, 99% of the reconstituted peptide, particularly of the reconstituted antigenic peptide, inserted into the lipid bilayer through its hydrophobic moieties, is present on the outer surface of the liposome.

In particular, 100% of the reconstituted peptide, particularly of the reconstituted antigenic peptide, inserted into the lipid bilayer through its hydrophobic moieties, is present on the surface of the liposome.

In one embodiment, the invention relates to the method of any one of the preceding embodiments, wherein the peptide, particularly of the antigenic peptide, is modified by addition of a fatty acid, a triglyceride, a diglyceride, a steroid, a sphingolipid, a glycolipid or a phospholipid.

In particular, the peptide, particularly of the antigenic peptide, is modified by addition of a fatty acid, particularly a fatty acid with a carbon back bone of at least 6 carbon atoms.

In a specific embodiment, the hydrophobic moiety is palmitic acid.

In still another embodiment, the invention relates to the method of any one of the preceding embodiments, wherein the peptide, particularly of the antigenic peptide, is further modified through pegylation using lipidated polyethylene glycol or a modified lipidated polyethylene glycol.

In particular, the polyethylene glycol or modified polyethylene glycol comprises between 8 to 150.000, particularly between 10 to 80.000, particularly between 10 to 10.000 or 8 to 5000, particularly between 2-1000, particularly between 5-500, particularly between 10-200 ethylene oxide moieties.

In particular, the PEG chain contains not more than n=45 ethylene oxide moieties, particularly between n=5 and n=40, more particularly between n=10 and n=30, and even more particularly n=10 ethylene oxide moieties.

In one embodiment, the invention relates to the method of any one of the preceding embodiments, wherein the peptide, particularly of the antigenic peptide, is modified by covalently attached palmitoylated amino acid residues, particularly between 2 and 4, more particularly 4 residues covalently attached to either the N- or the C-terminus of the peptide, particularly to the N- and the C-terminus of the peptide.

In a specific embodiment, the peptide, particularly of the antigenic peptide, is modified by 4 palmitoylated amino acid residues, two of which are covalently attached to the N- and C-terminus of the peptide, respectively.

In one embodiment, the invention relates to a liposome-based construct, particularly a liposome-based antigenic construct comprising a peptide, particularly an antigenic peptide, of interest modified through hydrophobic moieties reconstituted in a liposome obtainable by a method according to any of the preceding embodiment, wherein at least 70% of the reconstituted antigenic peptide is present on the outer surface of the liposome, wherein said peptide is inserted into the lipid bilayer through its hydrophobic moieties without the aid of any chemical reaction or additional molecule modifications by, for example, coupling a reactant on the external lipid surface of the liposome, or the use of pegylated peptides.

The peptide, particularly the antigenic peptide, is anchored and stabilized in the lipid bilayer of the liposome via its hydrophobic or lipophilic extension, which enters into weak interactions with the (phosphor)lipids of the liposomal bilayer, but does not form a strong covalent chemical bond with any of the constituents of the liposomal bilayer.

In particular, the invention relates to the liposome-based construct, particularly the liposome-based antigenic construct, of the preceding embodiment, wherein at least 70%, 71%, 72%, 73%, 74%, 75%, 76%, 77%, 78%, 79%, 80%, 81%, 82%, 83%, 84%, 85%, 86%, 87%, 89%, 90%, 91%, 92%, 93%, 94%, 95%, 96%, 97%, 98%, 99% of the reconstituted peptide, particularly of the reconstituted antigenic peptide, is present on the surface of the liposome.

In one embodiment, the invention relates to the liposome-based construct, particularly the liposome-based antigenic construct, of any one of the preceding embodiments, wherein at least 80% of the reconstituted peptide, particularly of the reconstituted antigenic peptide, is present on the outer surface of the liposome.

In one embodiment, the invention relates to the liposome-based construct, particularly the liposome-based antigenic construct, of any one of the preceding embodiments, wherein at least 85% of the reconstituted peptide, particularly of the reconstituted antigenic peptide, is present on the outer surface of the liposome.

In one embodiment, the invention relates to the liposome-based construct, particularly the liposome-based antigenic construct, of any one of the preceding embodiments, wherein at least 90% of the reconstituted peptide, particularly of the reconstituted antigenic peptide, is present on the outer surface of the liposome.

In one embodiment, the invention relates to the liposome-based construct, particularly the liposome-based antigenic construct, of any one of the preceding embodiments, wherein at least 100% of the reconstituted peptide, particularly of the reconstituted antigenic peptide, is present on the outer surface of the liposome.

In one embodiment, the invention relates to a liposome-based antigenic construct, of any one of the preceding embodiments, wherein said antigenic construct comprises an adjuvant reconstituted in the liposome.

In one embodiment, the invention relates to the antigenic construct of the preceding embodiment, wherein at least 70%, 71%, 72%, 73%, 74%, 75%, 76%, 77%, 78%, 79%, 80%, 81%, 82%, 83%, 84%, 85%, 86%, 87%, 89%, 90%, 91%, 92%, 93%, 94%, 95%, 96%, 97%, 98%, 99% of the reconstituted adjuvant is present on the outer surface of the liposome.

In one embodiment, the invention relates to the antigenic construct of any one of the preceding embodiments, wherein at least 80% of the reconstituted adjuvant is present on the outer surface of the liposome.

In one embodiment, the invention relates to the antigenic construct of any one of the preceding embodiments, wherein at least 85% of the reconstituted adjuvant is present on the outer surface of the liposome.

In one embodiment, the invention relates to the antigenic construct of any one of the preceding embodiments, wherein at least 90% of the reconstituted adjuvant is present on the outer surface of the liposome.

In one embodiment, the invention relates to the antigenic construct of any one of the preceding embodiments, wherein at least 100% of the reconstituted adjuvant is present on the outer surface of the liposome.

In one embodiment, the invention relates to the antigenic construct of any one of the preceding embodiments, wherein the adjuvant is selected from the group consisting of lipid A, detoxified lipid A, such as monophosphoryl or diphosphoryl lipid A, alum, Pam3CSK4, Pam3CAG or CpG, lipidated CpG, phosphorothioated PS-CpG-ODNs, CpG oligodeoxynucleotides (CpG-ODN) such as CpG-A, CpG-B or CpG-C. Further adjuvants, that may be used with the method according to the invention are, without intended to be limiting, aluminium phosphate or hydroxide (Al(OH)3, AlPO4), salts of calcium, iron or zirconium, QuilA, QS-21, trehalose dimycolate (TDM), lipoteichoic acid (purified from *Staphylococcus aureas*), DDAB (dimethyldioctadecylammonium (bromide salt)), MF59, L18-MDP & B30-MDP (hydrophobic muramyl-dipeptide derivatives), C12-iE-DAP (diaminopimelic acid)

In one embodiment, the invention relates to the liposome-based construct, particularly the liposome-based antigenic construct, of any one of the preceding embodiments, wherein the peptide, particularly the antigenic peptide, is modified by addition of a fatty acid, a triglyceride, a diglyceride, a steroid, a sphingolipid, a glycolipid or a phospholipid, particularly a fatty acid with a carbon back bone of at least 6 carbon atoms, but especially a palmitic acid.

In one embodiment, the invention relates to the liposome-based construct, particularly the liposome-based antigenic construct, of any one of the preceding embodiments, wherein the peptide, particularly the antigenic peptide, is modified through pegylation using lipidated polyethylene glycol or a modified lipidated polyethylene glycol.

In particular, the polyethylene glycol or modified polyethylene glycol comprises between 8 to 150.000, particularly between 10 to 80.000, more particularly between 10 to 10.000 or 8 to 5000, particularly between 2-1000, particularly between 5-500, particularly between 10-200 ethylene oxide moieties. In particular, the length of the PEG chain is not more than n=45, particularly between n=5 and n=40, more particularly between n=10 and n=30, and even more particularly n=10 ethylene oxide moieties.

In one embodiment, the invention relates to the liposome-based construct, particularly the liposome-based antigenic construct, of any one of the preceding embodiments, wherein the peptide, particularly the antigenic peptide, is modified by covalently attached palmitoylated amino acid residues, particularly between 2 and 4, more particularly 4 residues covalently attached to either the N- or the C-terminus of the peptide, particularly to the N- and the C-terminus of the peptide.

In a specific embodiment, the peptide, particularly the antigenic peptide, according to any one of the preceding embodiments, is modified by 4 palmitoylated amino acid residues, two of which are covalently attached to the N- and C-terminus of the peptide, respectively.

In still another embodiment of the invention a composition is provided comprising an construct, particularly an antigenic construct, according to any of the preceding embodiments.

In one embodiment, the composition of the preceding embodiment is a pharmaceutical composition comprising the construct, particularly the antigenic construct, of the invention in a therapeutically effective amount together with a pharmaceutically acceptable carrier.

Liposomes may be used as a delivery system for drugs with the aim to achieve selective targeting of "active" drug at disease sites such as tumors or inflamed tissues. Selective targeting requires a targeting device (antibody, receptor ligand, etc.) on the liposomal surface so that the liposome can recognize the target cells, bind to them selectively, and either be internalized by these cells or be broken down by either enzymatic hydrolysis or processes such as ultrasonic irradiation to release the drug near the cell surface so it will be taken up by the target cells.

In one embodiment of the invention, the pharmaceutical composition comprises a construct according to any one of the preceding embodiments, wherein the peptide has a targeting function and may be represented by an antibody or a functional part thereof, a receptor ligand, or any other peptide capable of recognizing and binding to an antigen, receptor, a specific tissue or a specific cell type.

In one aspect of the invention, the active drug provided encapsulated in the liposome-based construct according to the invention and as described herein may be a cytotoxic drug such as, for example, doxorubicin, paclitaxel, vincristine, or lurtotecan, an antifungal drug such as amphotericin B, a nucleic acid-based drug such as an antisense oligonucleotide or a plasmid DNA (pDNA) for systemic applications, a RNA, or a drug suitable for preventing inflammation or restenosis such as, for example, rapamycin, paclitaxel, actinomycin D, C-Myc antisense, dexamethasone, or a matrix metalloproteinase inhibitor.

In another aspect of the invention the active drug provided encapsulated in the liposome-based construct according to the invention and as described herein may be an artificial oxygen carrier such as encapsulated haemoglobin.

In another embodiment of the invention a method of inducing an immune response in a mammal is provided, comprising administering to said mammal a construct or a composition according to any of the preceding embodiments.

In still another embodiment, the invention relates to a method of producing an antibody comprising administering to a mammal an antigenic construct or a composition according to any of the preceding embodiments and isolating an antibody produced by said mammal. In a specific embodiment, this method further comprises the step of preparing a hybridoma cell from spleen cells obtained from the immunized mammal and isolating an antibody produced by said hybridoma cell.

In one embodiment, the invention relates to an antibody, particularly a polyclonal or a monoclonal antibody, produced by a method according to any one of the preceding embodiments.

In an alternative embodiment, the invention relates to use of a construct, particularly an antigenic construct, a composition or an antibody according to any of the preceding embodiments for therapeutic or preventive treatment of a mammal, particularly a human, in particular for the therapeutic or preventive vaccination of a mammal, particularly a human.

In a specific embodiment of the invention, the construct, particularly the antigenic construct, composition or antibody according to any of the preceding embodiments may be used in the therapeutic or preventive treatment, in particular in the therapeutic or preventive vaccination, of a mammal, particularly a human, particularly a mammal or a human suffering from a disease, disorder or condition relating to infectious diseases, CNS-related diseases, or diseases and disorders in the area of oncology or allergy, or inflammation, particularly from a disease, disorder or condition relating to a proteopathy, a disease involving protein misfolding and/or a disease involving protein accumulation or aggregation.

In still another embodiment, the invention relates to the use of an antibody of the invention in a method for detection or diagnosis of diseases, disorders or conditions, particularly of diseases, disorders or conditions relating to infectious diseases, CNS-related diseases, or diseases and disorders in the area of oncology or allergy, or inflammation, particularly of diseases or disorder relating to a proteopathy, a disease involving protein misfolding and/or a disease involving protein accumulation or aggregation.

In one embodiment, the invention relates to a diagnostic kit for use in a method for detection or diagnosis of diseases or disorders, particularly of diseases, disorders or conditions relating to infectious diseases, CNS-related diseases, or diseases and disorders in the area of oncology or allergy, or inflammation, particularly of diseases or disorders relating to a proteopathy, a disease involving protein misfolding and/or a disease involving protein accumulation or aggregation comprising an antibody of the invention.

In one embodiment, the present invention provides a pharmaceutical composition comprising the liposome-based construct, particularly the liposome-based antigenic construct, of the invention in a therapeutically effective amount together with a pharmaceutically acceptable carrier.

Suitable pharmaceutical carriers, diluents and/or excipients are well known in the art and include, for example, phosphate buffered saline solutions, water, emulsions such as oil/water emulsions, various types of wetting agents, sterile solutions, etc.

The liposome-based antigenic construct of the invention including antibodies produced therewith, particularly monoclonal antibodies and active fragments thereof, can be prepared in a physiologically acceptable formulation and may comprise a pharmaceutically acceptable carrier, diluent and/or excipient using known techniques. For example, the liposome-based antigenic construct of the invention including antibodies produced therewith, in particular, the monoclonal antibodies of the invention including any functionally equivalent antibodies or functional parts thereof, are combined with a pharmaceutically acceptable carrier, diluent and/or excipient to form a therapeutic composition. Suitable pharmaceutical carriers, diluents and/or excipients are well known in the art and include, for example, phosphate buffered saline solutions, water, emulsions such as oil/water emulsions, various types of wetting agents, sterile solutions, etc.

Formulation of the pharmaceutical composition according to the invention can be accomplished according to standard methodology know to those of ordinary skill in the art.

The compositions of the present invention may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal, interdermal, intraperitoneal, or parenteral (for example, intravenous, subcutaneous, or intramuscular) routes.

In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

It is well known to those of ordinary skill in the pertinent art that the dosage of the composition will depend on various factors such as, for example, the condition of being treated, the particular composition used, and other clinical factors such as weight, size, sex and general health condition of the patient, body surface area, the particular compound or composition to be administered, other drugs being administered concurrently, and the route of administration.

The composition according to the invention may be administered in combination with other compositions comprising a biologically active substance or compound such as, for example, a known compound used in the medication of a proteopathy, a disease involving protein misfolding and a disease involving protein accumulation or aggregation, tauopathies and/or of amyloidoses, a group of diseases and disorders associated with amyloid or amyloid-like protein such as the amyloid β protein involved in Alzheimer's Disease.

The other biologically active substance or compound may exert its biological effect by the same or a similar mechanism as the therapeutic composition according to the invention or by an unrelated mechanism of action or by a multiplicity of related and/or unrelated mechanisms of action.

The pharmaceutical composition according to the invention may be administered concomitantly with the other biologically active substance or substances, intermittently or sequentially. For example, the pharmaceutical composition according to the invention may be administered simultaneously with a first additional biologically active substance or sequentially after or before administration of the pharmaceutical composition. If an application scheme is chosen where more than one additional biologically active substance are administered together with the at least one pharmaceutical composition according to the invention, the compounds or substances may partially be administered simultaneously, partially sequentially in various combinations.

Generally, the other biologically active compound may include neutron-transmission enhancers, psychotherapeutic drugs, acetylcholine esterase inhibitors, calcium-channel blockers, biogenic amines, benzodiazepine tranquillizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists.

In particular, the biologically active agent or compound may comprise at least one compound selected from the group consisting of compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), secretase activators, [beta]- and 7-secretase inhibitors, tau proteins, neurotransmitter, β-sheet breakers, antiinflammatory molecules, "atypical antipsychotics" such as, for example clozapine, ziprasidone, risperidone, aripiprazole or olanzapine or cholinesterase inhibitors (ChEIs) such as tacrine, rivastigmine, donepezil, and/or galantamine and other drugs and nutritive supplements such as, for example, vitamin B 12, cysteine, a precursor of acetylcholine, lecithin, choline, Ginkgo biloba, acyetyl-L-carnitine, idebenone, propentofylline, or a xanthine derivative, together with a liposome-based antigenic construct of the invention including antibodies produced therewith, particularly monoclonal antibodies and active fragments thereof, and, optionally, a pharmaceutically acceptable carrier and/or a diluent and/or an excipient and instructions for the treatment of diseases.

In a further embodiment, the composition according to the invention may comprise niacin or memantine together with a liposome-based antigenic construct of the invention including antibodies produced therewith, particularly monoclonal antibodies and active fragments thereof, and, optionally, a pharmaceutically acceptable carrier and/or a diluent and/or an excipient.

In still another embodiment of the invention compositions are provided that comprise "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with the liposome-based antigenic construct of the invention including antibodies produced therewith, particularly monoclonal antibodies and active fragments thereof, and, optionally, a pharmaceutically acceptable carrier and/or a diluent and/or an excipient.

Other compounds that can be suitably used in compositions in addition to the binding peptide according to the invention, are those disclosed, for example, in WO 2004/058258 (see especially pages 16 and 17) including therapeutic drug targets (page 36-39), alkanesulfonic acids and alkanolsulfuric acid (pages 39-51), cholinesterase inhibitors (pages 51-56), NMDA receptor antagonists (pages 56-58), estrogens (pages 58-59), non-steroidal anti-inflammatory drugs (pages 60-61), antioxidants (pages 61-62), peroxisome proliferators-activated receptors (PPAR) agonists (pages 63-67), cholesterol-lowering agents (pages 68-75); amyloid inhibitors (pages 75-77), amyloid formation inhibitors (pages 77-78), metal chelators (pages 78-79), antipsychotics and anti-depressants (pages 80-82), nutritional supplements (pages 83-89) and compounds increasing the availability of biologically active substances in the brain (see pages 89-93) and prodrugs (pages 93 and 94), which document is incorporated herein by reference, but especially the compounds mentioned on the pages indicated above.

The dosage of the composition will depend on the condition being treated, the particular composition used, and other clinical factors such as weight, size and condition of the patient, body surface area, the particular compound or composition to be administered, other drugs being administered concurrently, and the route of administration.

Proteinaceous pharmaceutically active matter may be present in amounts between 1 ng and 10 mg per dose. Generally, the regime of administration should be in the range of between 0.1 µg and 10 mg of the antibody according to the invention, particularly in a range 1.0 µg to 1.0 mg, and more particularly in a range of between 1.0 µg and 100 µg, with all individual numbers falling within these ranges also being part of the invention. If the administration occurs through continuous infusion a more proper dosage may be in the range of between 0.01 µg and 10 mg units per kilogram of body weight per hour with all individual numbers falling within these ranges also being part of the invention.

In a specific embodiment of the invention, the antigenic construct according to any of the preceding embodiments or a composition comprising said antigenic construct in a therapeutically effective amount, is administered in repeated doses, in particular in 1 to 15 doses, more particularly in 2 to 10 doses, more particularly in 3 to 5 doses and even more particularly in 3 doses, in time intervals of between 1 week and 20 weeks, particularly in time intervals of between 1 and 10 weeks, particularly in time intervals of between 1 and 6 weeks, more particularly in time intervals of between 1 and 4 weeks, and even more particularly in time intervals of between 2 and 3 weeks. The immune response may be monitored by taking sera/plasma samples at a suitable time after boosting, particularly 3 to 10 days after boosting, more particularly 4 to 8 days after boosting and more particularly 7 days after boosting and determining the immunogenicity of the antigenic construct using known methodology, particularly one of the commonly used immunoassays such as, for example, an ELISA assay.

Administration will generally be parenterally, e.g. intravenously. Preparations for parenteral administration include sterile aqueous or non-aqueous solutions, The dosage of the composition will depend on the condition being treated, the particular composition used, and other clinical factors such as weight, size and condition of the patient, body surface area, the particular compound or composition to be administered, other drugs being administered concurrently, and the route of administration.

Non-aqueous solvents include, without being limited to, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, anti-oxidants, chelating agents, inert gases, etc.

The pharmaceutical composition may further comprise proteinaceous carriers such as, for example, serum albumin or immunoglobulin, particularly of human origin. Further biologically active agents may be present in the pharmaceutical composition of the invention dependent on the intended use.

When the binding target is located in the brain, certain embodiments of the invention provide for the liposome-based antigenic construct of the invention including antibodies produced therewith, particularly monoclonal antibodies and active fragments thereof, to traverse the blood-brain barrier. Certain neurodegenerative diseases are associated with an increase in permeability of the blood-brain barrier, such that the liposome-based antigenic construct of the invention including antibodies produced therewith, particularly monoclonal antibodies or active fragment thereof can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the liposome-based antigenic construct of the invention including antibodies produced therewith, particularly monoclonal antibodies, or active fragment thereof across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9: 398-406 (2002)) and implanting a delivery device in the brain (see, e.g., Gill et al., Nature Med. 9: 589-595 (2003); and Gliadel Wafers™, Guildford Pharmaceutical). Methods of creating openings in the barrier include, but are not limited to, ultrasound (see, e.g., U.S. Patent Publication No. 200210038086), osmotic pressure (e.g., by administration of hypertonic mannitol (Neuwelt, E. A., Implication of the Blood-Brain Barrier and its Manipulation, Vols 1 & 2, Plenum Press, N.Y. (1989))), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the binding peptide or antigen-binding fragment (see, e.g., U.S. Patent Publication No. 2003/0083299).

Lipid-based methods of transporting the liposome-based antigenic construct of the invention including antibodies produced therewith, particularly monoclonal antibodies, or an active fragment thereof across the blood-brain barrier include, but are not limited to, encapsulating said molecules in liposomes that are coupled to active fragments that bind to receptors on the vascular endothelium of the blood-brain barrier (see, e.g., U.S. Patent Application Publication No. 20020025313), and coating the liposome-based antigenic construct of the invention including antibodies produced therewith, particularly monoclonal antibodies, or active fragment thereof in low-density lipoprotein particles (see, e.g., U.S. Patent Application Publication No. 20040204354) or apolipoprotein E (see, e.g., U.S. Patent Application Publication No. 20040131692).

Receptor and channel-based methods of transporting the liposome-based antigenic construct of the invention including antibodies produced therewith, particularly monoclonal antibodies, or active fragment thereof across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

In a further embodiment the present invention provides methods and kits for the detection and diagnosis of diseases, disorders or conditions, particularly of diseases, disorders or conditions relating to infectious diseases, CNS-related diseases, or diseases and disorders in the area of oncology or allergy, particularly of diseases, disorders or conditions relating to a proteopathy, a disease involving protein misfolding and/or a disease involving protein accumulation or aggregation.

Further, the present invention provides methods and kits for diagnosing a predisposition to diseases, disorders or conditions, particularly to diseases, disorders or conditions relating to infectious diseases, CNS-related diseases, or diseases and disorders in the area of oncology or allergy, particularly to diseases, disorders or conditions relating to a proteopathy, a disease involving protein misfolding and/or a disease involving protein accumulation or aggregation, or for monitoring minimal residual disease in a patient or for predicting responsiveness of a patient to a treatment with a liposome-based antigenic construct according to the invention including antibodies, particularly monoclonal antibodies and active fragments thereof, or a composition according to the invention and as described herein in the various embodiments. These methods include known immunological methods commonly used for detecting or quantifying substances in biological samples or in an in situ condition.

Diagnosis of a disease, disorder or condition, particularly of a disease, disorder or condition relating to infectious diseases, CNS-related diseases, or diseases and disorders in the area of oncology or allergy, particularly of a disease, disorder or condition relating to a proteopathy, a disease involving protein misfolding and/or a disease involving protein accumulation or aggregation or of a predisposition to such a disease or condition in a subject, particularly a mammal, more particularly a human, may be achieved by detecting the immunospecific binding of an antibody according to the invention, particularly of a monoclonal antibody or an active fragment thereof, to an epitope in a protein region causative for the disease in a sample or in situ, which includes bringing the sample or a specific body part or body area suspected to contain the disease-causing protein or protein aggregate into contact with an antibody which binds to an epitope in region of said protein causative for the disease, allowing the antibody to bind to the protein to form an immunologic complex, detecting the formation of the immunologic complex and correlating the presence or absence of the immunologic complex with the presence or absence of the disease-causing protein or protein aggregate in the sample or specific body part or area, optionally comparing the amount of the immunologic complex to a normal control value, wherein an increase in the amount of the immunologic complex compared to a normal control value indicates that the subject is suffering from or is at risk of developing an disease or condition relating to a proteopathy, a disease involving protein misfolding and/or a disease involving protein accumulation or aggregation.

Monitoring minimal residual disease in a subject, particularly a mammal, more particularly a human, following treatment with a liposome-based antigenic construct according to the invention including antibodies, particularly monoclonal antibodies and active fragments thereof, or a composition according to the invention and as described herein in the various embodiments, may be achieved by detecting the immunospecific binding of an antibody according to the invention, particularly of a monoclonal antibody or an active fragment thereof, to an epitope in a protein region causative for the disease in a sample or in situ, which includes bringing the sample or a specific body part or body area suspected to contain the disease-causing protein or protein aggregate into contact with an antibody which binds to an epitope in region of said protein causative for the disease, allowing the antibody to bind to the protein to form an immunologic complex, detecting the formation of the immunologic complex and correlating the presence or absence of the immunologic complex with the presence or absence of the disease-causing protein or protein aggregate in the sample or specific body part or area, optionally comparing the amount of said immunologic complex to a normal control value, wherein an increase in the amount of said immunologic complex compared to a normal control value indicates that the subject may still suffer from a minimal residual disease.

Predicting responsiveness of a subject, particularly a mammal, more particularly a human, to a treatment with a liposome-based antigenic construct according to the invention including antibodies, particularly monoclonal antibodies and active fragments thereof, or a composition according to the invention and as described herein in the various embodiments, may be achieved by detecting the immunospecific binding of a binding peptide, particularly of a monoclonal antibody or an active fragment thereof to an epitope in a protein region causative for the disease in a sample or in situ, which includes bringing the sample or a specific body part or body area suspected to contain the disease-causing protein or protein aggregate into contact with an antibody which binds to an epitope in region of said protein causative for the disease, allowing the antibody to bind to the protein to form an immunologic complex, detecting the formation of the immunologic complex and correlating the presence or absence of the immunologic complex with the presence or absence of the disease-causing protein or protein aggregate in the sample or specific body part or area, optionally comparing the amount of said immunologic complex before and after onset of the treatment, wherein an decrease in the amount of said immunologic complex indicates that said patient has a high potential of being responsive to the treatment.

In particular, the disease or condition to be detected in the diagnostic methods reported herein before and/or disease or condition to be therapeutically or preventively treated by using the antigenic construct and/or antibody reported herein before are particularly diseases or conditions selected from the group consisting of AA amyloidosis, AH (heavy chain) amyloidosis, AL (light chain) amyloidosis, Alexander disease, Alzheimer's disease, amyotrophic lateral sclerosis, aortic medial amyloidosis, apoA1 amyloidosis, apoA2 amyloidosis, apoA4 amyloidosis, aortic medial amyloidosis, CADASIL, cardiac atrial amyloidosis, cataract, cerebral amyloid angiopathy, corneal lactoferrin amyloidosis, critical illness myopathy, cutaneous lichen amyloidosis, cystic fibrosis, dialysis amyloidosis, Familial amyloidotic neuropathy, familial British dementia, familial Danish dementia, familial visceral amyloidosis, fibrinogen amyloidosis, Finnish hereditary amyloidosis, frontotemporal lobar dementia, Glaucoma, hereditary cerebral hemorrhage with amyloidosis—Dutch type, hereditary cerebral hemorrhage with amyloidosis—Icelandic type, Huntington's disease and other triplet disorders, hereditary lattice corneal dystrophy, inclusion body myositis/myopathy, lysozyme amyloidosis, Mallory bodies, medullary thyroid carcinoma, Odontogenic (Pindborg) tumor amyloid, Parkinson's disease, pituitary prolactinoma, primary systemic amyloidosis, primary cutaneous amyloidosis, prion disease, pulmonary alveolar proteinosis, retinal ganglion cell degeneration in glaucoma, prion disease, seminal vesicle amyloid, seipinopathy, senile systemic amyloidosis, serpinopathy, sickle cell disease, synucleinopathy, tauopathy, and type 2 diabetes, or inflammation.

Biological samples that may be used in the diagnosis of such a disease or condition, for diagnosing a predisposition to such a disease or condition, or for monitoring minimal residual disease in a patient or for predicting responsiveness of a patient to a treatment with a liposome-based antigenic construct according to the invention including antibodies, particularly monoclonal antibodies and active fragments thereof, or a composition according to the invention and as described herein in the various embodiments, are, for example, fluids such as serum, plasma, saliva, gastric secretions, mucus, cerebrospinal fluid, lymphatic fluid and the like or tissue or cell samples obtained from an organism such as neural, brain, cardiac or vascular tissue. For determining the presence or absence of the disease-causing protein or protein aggregate in a sample, any immunoassay known to those of ordinary skill in the art may be used such as, for example, assays which utilize indirect detection methods using secondary reagents for detection, ELISA's and immunoprecipitation and agglutination assays. A detailed description of these assays is, for example, given in Harlow and Lane, Antibodies: A Laboratory Manual (Cold Spring Harbor Laboratory, New York 1988 555-612, WO96/13590 to Maertens and Stuyver, Zrein et al. (1998) and WO96/29605.

For in situ diagnosis, the binding peptide according to the invention including antibodies, particularly monoclonal antibodies and active fragments thereof, of the invention or any active and functional part thereof may be administered to the organism to be diagnosed by methods known in the art such as, for example, intravenous, intranasal, intraperitoneal, intracerebral, intraarterial injection such that a specific binding between an antibody according to the invention with an eptitopic region on the disease-causing protein or protein aggregate may occur. The binding peptide/antigen complex may conveniently be detected through a label attached to the binding peptide according to the invention including antibodies, particularly monoclonal antibodies, or a functional fragment thereof or any other art-known method of detection.

The immunoassays used in diagnostic applications or in applications for diagnosing a predisposition to protein-associated disease or condition, including a proteopathy, a disease involving protein misfolding and/or a disease involving protein accumulation or aggregation, or for monitoring minimal residual disease in a patient or for predicting responsiveness of a patient to a treatment with a liposome-based antigenic construct according to the invention including antibodies, particularly monoclonal antibodies and active fragments thereof, or a composition according to the invention and as described herein in the various embodiments, typically rely on labelled antigens, binding peptides, or secondary reagents for detection. These proteins or reagents can be labelled with compounds generally known to those of ordinary skill in the art including enzymes, radioisotopes, and fluorescent, luminescent and chromogenic substances including, but not limited to colored particles, such as colloidal gold and latex beads. Of these, radioactive labelling can be used for almost all types of assays and with most variations. Enzyme-conjugated labels are particularly useful when radioactivity must be avoided or when quick results are needed. Fluorochromes, although requiring expensive equipment for their use, provide a very sensitive method of detection. Binding peptides useful in these assays are those disclosed claimed herein including antibodies, particularly monoclonal antibodies, polyclonal antibodies, and affinity purified polyclonal antibodies.

Alternatively, the antibodies of the invention, particularly monoclonal antibodies and active fragments thereof, may be labelled indirectly by reaction with labelled substances that have an affinity for immunoglobulin, such as protein A or G or second antibodies. The antibodies according to the invention, particularly monoclonal antibodies and active fragments thereof, may be conjugated with a second substance and detected with a labelled third substance having an affinity for the second substance conjugated to the antibody. For example, the antibodies according to the invention, particularly monoclonal antibodies and active fragments thereof, may be conjugated to biotin and the binding peptide/biotin conjugate detected using labelled avidin or streptavidin. Similarly, the binding peptide may be conjugated to a hapten and the binding peptide/hapten conjugate detected using labelled anti-hapten binding peptide.

Those of ordinary skill in the art will know of these and other suitable labels which may be employed in accordance with the present invention. The binding of these labels to the antibodies or fragments thereof can be accomplished using standard techniques commonly known to those of ordinary skill in the art. Typical techniques are described by Kennedy, J. H., et al., 1976 (Clin. Chim. Acta 70:1-31), and Schurs, A. H. W. M., et al. 1977 (Clin. Chim Acta 57:1-40). Coupling techniques mentioned in the latter are the glutaraldehyde method, the periodate method, the dimaleimide method, and others, all of which are incorporated by reference herein.

Current immunoassays utilize a double antibody method for detecting the presence of an analyte, wherein, the antibody is labeled indirectly by reactivity with a second antibody that has been labeled with a detectable label. The second antibody is preferably one that binds to antibodies of the animal from which the monoclonal antibody is derived. In other words, if the monoclonal antibody is a mouse antibody, then the labeled, second antibody is an anti-mouse antibody. For the antibody to be used in the assay described herein, this label is preferably an antibody-coated bead, particularly a magnetic bead. For the antibody to be employed in the immunoassay described herein, the label is preferably a detectable molecule such as a radioactive, fluorescent or an electrochemiluminescent substance.

An alternative double antibody system, often referred to as fast format systems because they are adapted to rapid determinations of the presence of an analyte, may also be employed within the scope of the present invention. The system requires high affinity between the antibody and the analyte. According to one embodiment of the present invention, the presence of the disease-causing protein or protein aggregate is determined using a pair of antibodies, each specific for said protein. One of said pairs of antibodies is referred to herein as a "detector antibody" and the other of said pair of antibodies is referred to herein as a "capture antibody". The monoclonal antibody of the present invention can be used as either a capture antibody or a detector antibody. The monoclonal antibody of the present invention can also be used as both capture and detector antibody, together in a single assay.

One embodiment of the present invention thus uses the double antibody sandwich method for detecting the disease-causing protein or protein aggregate in a sample of biological fluid. In this method, the analyte (amyloid protein) is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte.

Exemplary solid phase substances include, but are not limited to, microtiter plates, test tubes of polystyrene, magnetic, plastic or glass beads and slides which are well known in the field of radioimmunoassay and enzyme immunoassay. Methods for coupling antibodies to solid phases are also well known to those of ordinary skill in the art. More recently, a number of porous material such as nylon, nitrocellulose, cellulose acetate, glass fibers and other porous polymers have been employed as solid supports.

The present invention also relates to a diagnostic kit for detecting the disease-causing protein or protein aggregate in a biological sample comprising a composition as defined above. Moreover, the present invention relates to the latter diagnostic kit which, in addition to a composition as defined above, also comprises a detection reagent as defined above. The term "diagnostic kit" refers in general to any diagnostic kit known in the art. More specifically, the latter term refers to a diagnostic kit as described in Zrein et al. (1998).

It is still another object of the present invention to provide novel immunoprobes and test kits for detection and diagnosis of diseases and conditions relating to a proteopathy, a disease involving protein misfolding and/or a disease involving protein accumulation or aggregation, comprising antibodies according to the present invention. For immunoprobes, the antibodies are directly or indirectly attached to a suitable reporter molecule, e.g., an enzyme or a radionuclide. The test kit includes a container holding one or more antibodies according to the present invention and instructions for using the antibodies for the purpose of binding to the disease-causing antigen to form an immunologic complex and detecting the formation of the immunologic complex such that presence or absence of the immunologic complex correlates with presence or absence of the disease-causing protein or protein aggregate.

DEFINITIONS

As used in this specification and the appended claims, the singular forms "a", "an", and "the" include plural referents unless the context clearly dictates otherwise. Thus, for example, reference to "a peptide" includes one or more peptides.

The terms "essentially", "about", "approximately" and the like in connection with an attribute or a value particularly also define exactly the attribute or exactly the value, respectively.

Furthermore, in the claims the word "comprising" does not exclude other elements or steps. A single step may fulfil the functions of several features recited in the claims.

The terms "polypeptide", "peptide", and "protein", as used herein, are interchangeable and are defined to mean a biomolecule composed of two or more amino acids linked by a peptide bond.

The term "peptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the peptide, or to the alpha-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

Typically, the amino acids making up a peptide are numbered in order, starting at the amino terminal and increasing in the direction toward the carboxy terminal of the peptide. Thus, when one amino acid is said to "follow" another, that amino acid is positioned closer to the carboxy terminal of the peptide than the preceding amino acid.

The term "residue" is used herein to refer to an amino acid that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

The term "modified peptide" is used herein to refer to any peptide which is modified through addition of hydrophobic moieties such that the modified peptide is available in a micellar form. The peptide may have a targeting function and thus may refer to an antibody or a binding fragment of an antibody, a ligand, a antigen, a receptor, a carrier protein, or any other protein or peptide capable of recognizing and binding to an antigen, receptor, tissue or cell type including fibroblasts, epithelial cells, endothelial cells, blood cells, tumor cells, etc. In particular, the modified peptide may be capable of targeting the liposome to tumor tissue or tumor cells. The modified peptide for use in the liposomal constructs of the invention as described herein in various embodiments may also be a peptide targeting the vasculature of solid tumors.

In one aspect, the modified peptide for use in the liposomal constructs of the invention as described herein in various embodiments is a targeting peptide which serves as a recognition component in protein-protein interactions such as receptor-ligand interactions.

In one aspect, the modified peptide for use in the liposomal constructs of the invention as described herein in various embodiments is an antigenic peptide as described herein below.

In another aspect, the modified peptide for use in the liposomal constructs of the invention as described herein in various embodiments is a RGD-peptide, a somatostatin, a chemotactic peptide, a vasoactive intestinal peptide, as well as a mimetic thereof. Generally, these peptides bind to target cells with a ligand-receptor association at high affinity and enter the intercellular compartments through receptor-mediated endocytosis (for further information see US20030229013).

In still another aspect, the modified peptide for use in the liposomal constructs of the invention as described herein in various embodiments is an antibody, particularly a monoclonal antibody or antibody fragment such as, for example, an antibody or antibody fragment which has a specific recognition to a B-cell or a T-cell epitope, as has been described in U.S. Pat. No. 5,620,689. For example, the antibody can be one that recognizes the B-cell epitopes CD19, CD20, CD22 or CD77. The antibody can be one that recognizes the T-cell epitopes CD4, CD7 or CD8.

The targeting functionality of the peptides embedded on the outer surface of the liposomes can be used for delivering small biologically active molecules such as therapeutic agents and/or oligonucleotides. The delivery specificity is confined by the liposomal peptide binding capacity to a restricted cell type.

Therapeutic agents include natural and synthetic compounds, particularly compounds that have anti-arthritic, anti-arrhythmic, anti-bacterial, anticholinergic, anticoagulant, antidiuretic, antidote, antiepileptic, antifungal, anti-inflammatory, antimetabolic, antimigraine, antineoplastic, antiparasitic, antipyretic, antiseizure, antisera, antispasmodic, analgesic, anesthetic, beta-blocking, biological response modifying, bone metabolism regulating, cardiovascular, diuretic, enzymatic, fertility enhancing, growth-promoting, hemostatic, hormonal, hormonal suppressing, hypercalcemic alleviating, hypocalcemic alleviating, hypoglycemic alleviating, hyperglycemic alleviating, immunosuppressive, immunoenhancing, muscle relaxing, neurotransmitting, parasympathomimetic, sympathominetric plasma extending, plasma expanding, psychotropic, thrombolytic or vasodilating activities.

In particular, the modified peptide to be used on a liposome according to the invention and as described herein in various embodiments may be a tumor-targeting peptide embedded on the outer surface of a liposome comprising entrapped therein an anti-tumor compound to form a therapeutic composition. The anti-tumor compound may be a chemotherapeutic and/or cytotoxic agent such as a compound that stops DNA building block synthesis (e.g., methotrexate, fluorouracil, hydroxyurea, and mercaptopurine), a compound that directly damages DNA (e.g., anthracycline antibiotics such as daunorubicin, doxorubicin, epirubicin and idarubicin, and analogs therefor such as epirubidin and mitoxantrone, or etoposide and platinum compounds such as cisplatin, carboplatin, ormaplatin, oxaliplatin, zeniplatin, enloplatin, lobaplatin, spiroplatin, ((−)-(R)-2-aminomethyl-pyrrolidine (1,1-cyclobutane dicarboxylato)platinum) (DWA2114R), (SP-4-3(R)-1,1-cyclobutane-dicarboxylato (2-)-(2-methyl-1,4-butanediamine-N,N')platinum) (CI-973), nedaplatin (254-S) and (bis-acetato-ammine-dichloro-cyclohexylamine-platinum(IV)) (JM-216) (Weiss, R. B., et al., Drugs, 46(3): 360-377 (1993)), a compound that affects mitotic spindle synthesis or breakdown (e.g., a vinca alkaloid selected from the group consisting of vincristine, vinblastine, vinleurosine, vinrodisine, vinorelbine and vindesine or pacitaxel), or a compound that disrupts angiogenesis (e.g., anti-VEGF antibody, angiostatin, endostatin, tumstatin, and TNF[alpha]). Alternatively, the anti-tumor drug can be a topoisomerase I inhibitor, such as camptothecin and its analogues or a radiotherapy agent (e.g., <90>Y, <125>I, <188>Re, <111>In DTPA, or <131>I sodium iodide).

The entrapped biologically active molecule may also be a nucleic acid such as, for example, an antisense oligonucleotide or ribozyme, a siRNA or a plasmid containing a therapeutic gene which when internalized by the target cells achieves expression of the therapeutic gene to produce a therapeutic gene product for the treatment of, for example, viral, malignant and inflammatory diseases and conditions, such as, cystic fibrosis, adenosine deaminase deficiency and AIDS. In on aspect, the oligonucleotide may be a tumor suppressor gene, such as APC, DPC4, NF-1, NF-2, MTS1, RB, p53, WT1, BRCA1, BRCA2 and VHL, to be used for the treatment of cancer (for further information see US 2010119444).

In one aspect of the invention, the peptide to be used on a liposome according to the invention and as described herein in various embodiments may be a peptide targeting the vasculature of solid tumors. Exemplary vascular targeting agents (VTAs) are described in U.S. Pat. Nos. 5,855,866, 5,965,132, 6,261,535, 6,051,230 and 6,451,312, which describe the targeted delivery of anti-cellular agents and toxins to markers of tumor vasculature.

Another effective version of the vascular targeting approach is to target a coagulation factor to a marker expressed or adsorbed within the tumor vasculature or stroma (Huang et al., 1997; U.S. Pat. Nos. 6,093,399, 6,004,555, 5,877,289, and 6,036,955).

In another aspect of the invention, the peptide to be used on a liposome according to the invention and as described herein in various embodiments may be an antibody, particularly a monoclonal antibody or antibody fragment such as, for example, an antibody or antibody fragment which has a specific recognition to a B-cell or a T-cell epitope and the entrapped biologically active molecule may doxorubicin, vincristine, lomustine, interferon, melphalan, cyclophosphamide, prednisone, chlorambucil, carmustin and dexamethasone, for the treatment of hematological disorders.

The term "antigenic peptide" or an "antigenic peptide of interest" relates to any peptide capable, upon administration to a mammal, particularly a human, of generating an immune response in said mammal or human. In a specific aspect of the invention, an antigenic peptide relates to a peptide derived from an amyloid protein or amyloid-like protein such as, for example prion protein, tau protein, alpha-synuclein, huntingtin, amylin or an amyloid-3 or a combination of one or more of the above peptides.

An Aβ antigenic peptide fragment may correspond to the N-terminal part of the Aβ peptide, particularly to the N-terminal part comprising at least 5, particularly at least 6, particularly at least 7, particularly at least 8, particularly at least 9, particularly at least 10, particularly at least 11, particularly at least 12, particularly at least 13, particularly at least 14, particularly all, amino acid residues from the Aβ1-15 fragment or the Aβ1-16 fragment.

The Aβ antigenic peptide fragment may further correspond to the N-terminal part of the Aβ peptide comprising at least 5, particularly at least 6, particularly at least 7, particularly at least 8, particularly at least 9, particularly at least 10, particularly at least 11, particularly at least 12, particularly at least 13, particularly at least 14, particularly at least 15, particularly all, amino acid residues from the Aβ1-16 fragment, the Aβ1-17 fragment, the Aβ1-18 fragment, the Aβ1-19 fragment, the Aβ1-20 fragment, the Aβ1-22 fragment, the Aβ1-23 fragment, the Aβ1-24 fragment, the Aβ1-25 fragment or, the Aβ1-26 fragment, or the 3-15 Aβ fragment.

The Aβ antigenic peptide fragment may further correspond to the C-terminal part of the Aβ peptide comprising at least 5, particularly at least 6, particularly at least 7, particularly at least 8, particularly at least 9, particularly at least 10, particularly at least 11, particularly at least 12, particularly at least 13, particularly at least 14, particularly at least 15, particularly all amino acid residues from the Aβ20-40 or Aβ20-42 fragment, the Aβ21-40 or Aβ21-42 fragment, the Aβ22-40 or Aβ22-42 fragment, the Aβ23-40 or Aβ23-42 fragment, the Aβ24-40 or Aβ24-42 fragment, the Aβ25-40 or Aβ25-42 fragment, the Aβ26-46 or Aβ27-42 fragment, or the Aβ27-40 or Aβ27-42 fragment, or the Aβ29-40.

In one aspect, the Aβ antigenic peptide fragment may correspond to the middle part of the Aβ peptide comprising at least 5, particularly at least 6, particularly at least 7, particularly at least 8, particularly at least 9, particularly at least 10, particularly at least 11, particularly at least 12, particularly at least 13, particularly at least 14, particularly at least 15, particularly all amino acid residues from the Aβ15-35, particularly the Aβ20-35 fragment.

In another aspect of the invention, the full length Aβ1-39, Aβ1-40, or Aβ1-42 fragment may be used within a construct according to the invention and as described herein.

In certain aspects of the invention, the Aβ antigenic peptide fragment as disclosed herein may contain one or more modified or non-natural amino acid residues.

In certain embodiments of the invention, the use of Aβ antigenic peptide fragments is contemplated consisting of a single or repetitive stretch of between 13 and 15 contiguous amino acid residues from the N-terminal part of the Aβ peptide, particularly fragments, wherein said contiguous stretch of 13 to 15 amino acid residues is obtained from the N-terminal fragment 1-16 or 1-17 of the Aβ peptide, particularly from the N-terminal part of the Aβ peptide selected from the group consisting of residues 1-15, 1-14, and 1-13, particularly consisting of $A\beta_{1-15}$ peptide antigen as given in SEQ ID NO: 1 and $A\beta_{1-16(\Delta 14)}$ as given in SEQ ID NO: 3 disclosed in WO 2007/068411.

In particular, an antigenic peptide derived from an amyloid protein or amyloid-like protein may be a peptide such as an Aβ peptide, specifically an Aβ peptide fragment from the N-terminal part of the Aβ peptide, but particularly an Aβ peptide fragment consisting of amino acid residues selected from the group consisting of 1-15, 2-15, 3-15, 1-14, 2-14, 1-13; 1-16(Δ2), 1-16(Δ4), 1-16(Δ5), 1-16(Δ6), 1-16(Δ8), 1-16(Δ9), 1-16(Δ10); 1-16(Δ12), 16(Δ13), 16(Δ14), 1-16(Δ15), 1-15(Δ2), 1-15(Δ4), 1-15(Δ5), 1-15(Δ6), 1-15(Δ8), 1-15(Δ9), 1-15(Δ10); 1-15(Δ12), 15(Δ13), 15(Δ14), particularly an $A\beta_{1-16(\Delta 15)}$ peptide antigen, more particularly a $A\beta_{1-16(\Delta 14)}$ or $A\beta_{1-16(\Delta 13)}$ peptide antigen, even more particularly a $A\beta_{1-14}$ peptide antigen, specifically a $A\beta_{1-15}$ peptide antigen, but especially an Aβ peptide fragment consisting of amino acid residues 1-15 as given in which antigenic peptide is presented attached to, or incorporated or reconstituted in a carrier such as, for example, a vesicle, a particulate body or molecule but, particularly, a liposome.

| DESCRIPTION | VACCINE | SEQUENCE |
| --- | --- | --- |
| Ac 1-15: Acetyl Abeta 1-15 encapsulated in liposomes (control for peptide display) | ACI-16 | H-K(Ac)K(Ac)-DAEFRHDSGYEVHHQ-K(Ac)K(Ac)-OH (SEQ ID NO: 11) |
| Vaccine with tetra-palmitoylated Abeta peptide | ACI-24 | H-K(Pal)K(Pal)-DAEFRHDSGYEVHHQ-K(Pal)K(Pal)-OH (SEQ ID NO: 12) |

Alternatively, the "antigenic peptide of interest" may be also a phosphor-tau protein being designed as antigen for vaccine development or a mixture of Aβ peptide antigen as described herein in the various embodiments above and the phosphor-tau protein according to the irrespective need. Such phosphor-tau protein may be represented by one or more of the following sequences (T5 to T11) depicted in the table below. A previously used immunogenic peptide may be used as a control (Asuni et al., 2007).

| DESCRIPTION | VACCINE | SEQUENCE |
| --- | --- | --- |
| T5 Control sequence: Tau 379-408 [pS396, pS404] | ACI-37 | RENAKAKTDHGAEIVYKS(p)PVVSGDTS(p)PRHL (n = 30) (SEQ ID NO: 1) |
| T1: Tau 5-20 [pY18] | ACI-33 | RQEFEVMEDHAGTY(p)GL (n = 16) (SEQ ID NO: 2) |
| T8: Tau 206-221 [pT212, pS214] | ACI-39 | PGSRSRT(p)PS(p)LPTPPTR (n = 16) (SEQ ID NO: 3) |
| T9: Tau 196-211 [pS202, pT205] | ACI-40 | GYSSPGS(p)PGT(p)PGSRSR (n = 16) (SEQ ID NO: 4) |
| T8: Tau 206-221 [pT212, pS214] and T9: Tau 196-211 [pS202, pT205] | ACI-41 | PGSRSRT(p)PS(p)LPTPPTR (n = 16) (SEQ ID NO: 3) and GYSSPGS(p)PGT(p)PGSRSR (n = 16) (SEQ ID NO: 4) |
| T3: Tau 393-408 [pS396, pS404] | ACI-35 | VYKS(p)PVVSGDTS(p)PRHL (n = 16) (SEQ ID NO: 5) |
| T4: Tau 401-418 [pS404, pS409] | ACI-36 | GDTS(p)PRHLS(p)NVSSTGSID (n = 18) (SEQ ID NO: 6) |
| T2: Tau 200-216 [pS202 + pT205 & pT212 + pS214] | ACI-34 | PGS(p)PGT(p)PGSRSRT(p)PS(p)LP (n = 17) (SEQ ID NO: 7) |
| T10: Tau 407-418 [pS409] | ACI-42 | HLS(p)NVSSTGSID (n = 12) (SEQ ID NO: 8) |
| T11: Tau 399-408 [pS404] | ACI-43 | VSGDTS(p)PRHL (n = 10) (SEQ ID NO 9) |

The peptide or antigenic peptide according to the invention is modified through lipophilic or hydrophobic moieties, that facilitate insertion into the lipid bilayer of the liposome carrier/immune adjuvant, particularly by lipophilic or hydrophobic moieties including, but not limited to, a fatty acid, a triglyceride, diglyceride, steroid, sphingolipid, glycolipid or a phospholipid, but especially a fatty acid, a triglyceride or a phospholipid, wherein, for example, the fatty acid carbon back bone has at least 6 carbon atoms which functions as an anchor for the peptide in the liposome bilayer and has a dimension that leads to the peptide being positioned and stabilized in close proximity to the liposome surface. Particularly, the lipophilic or hydrophobic moiety is a fatty acid with a carbon backbone of at least approximately 14 carbon atoms and up to approximately 24 carbon atoms, with each individual number of carbon atom falling within this range also being part of the present invention. More particularly, the lipophilic or hydrophobic moiety has a carbon backbone of at least 14 carbon atoms, but especially 16 carbon atoms. Examples of hydrophobic moieties include, but are not limited to, palmitic acid, stearic acid, myristic acid, lauric acid, oleic acid, linoleic acid, and linolenic acid, cholesterol or 1,2-distearoyl-sn-glycero-3-phosphatidylethanolamine (DSPE).

In still a further embodiment of the invention the hydrophobic moiety is palmitic acid. The liposome preparation may in addition contain an adjuvant such as, for example, lipid A, alum, calcium phosphate, interleukin 1, and/or microcapsules of polysaccharides and proteins, but particularly a detoxified lipid A, such as monophosphoryl or diphosphoryl lipid A, alum, Pam3CSK4, Pam3CAG, CpG, lipidated CpG, phosphorothioated PS-CpG-ODNs, or CpG oligodeoxynucleotides (CpG-ODN) such as CpG-A, CpG-B or CpG-C.

Accordingly, the adjuvant for use in the liposomal constructs of the invention as described herein in various embodiments is a CpG oligodeoxynucleotides (CpG-ODN) such as CpG-A, CpG-B or CpG-C. The oligonucleotide-modified CpGs can act as a synthetic stimulus that induces large amounts of the anti-viral cytokines type I interferons upon viral infection or induces—Toll-like receptors (TLRs) over-expression.

The modification of the peptide, particularly the antigenic peptide, according to the invention occurs via lipidation of the amino acid residue located at the N-terminal and/or C-terminal end of the peptide molecule, or, in the alternative, at an amino acid residue added to the N- or C-terminal end of the peptide molecule. Addition of amino acid residues may become necessary, if the native peptide sequence does not provide an N- and/or C-terminal amino acid suitable for modification via lipidation. Alternatively, the second or third amino acid residue at the N- and/or C-terminal end of the peptide fragment may become lipidated as part of the modification process.

When preformed, empty liposomes are used, the peptide, particularly the antigenic peptide, according to the invention is modified to provide a hydrophobic tail(s) that inserts into the liposome membrane as it is formed. Additionally, the peptide can be modified to contain a hydrophobic tail so that it can be inserted into the liposome.

The antigenic constructs of the present invention generally comprise peptides modified to enhance antigenic effect wherein such peptides may be modified by palmitic acid as described herein before in the various embodiments, poly-amino acids (eg poly-glycine, poly-histidine), poly-saccharides (eg polygalacturonic acid, polylactic acid, polyglycolide, chitin, chitosan), synthetic polymers (polyamides, polyurethanes, polyesters) or co-polymers (eg. poly(methacrylic acid) and N-(2-hydroxy) propyl methacrylamide) and the like, or may be further modified via pegylation (using polyethylene glycol or modified polyethylene glycol).

In the "liposome-based construct" according to the present invention, the liposome may have a dual function in that it can be used as a carrier comprising reconstituted in the lipid bilayer a modified peptide of the invention and as described herein before in the various embodiments and, at the same time, function as a delivery system for an active drug or compound. In case of an "liposome-based antigenic construct" according to the present invention, the liposome may have a further function as an adjuvant to increase or stimulate the immune response within the target animal or human to be treated with a therapeutic vaccine. It is also to be understood that the liposome-based antigenic construct compositions of the present invention can further comprise additional adjuvants including, but not limited to, keyhole limpet hemocyanin (KLH), bovine serum albumin (BSA) and other adjuvants such as, for example, lipid A, alum, calcium phosphate, interleukin 1, and/or microcapsules of polysaccharides and proteins, but particularly a detoxified lipid A, such as monophosphoryl or diphosphoryl lipid A, or alum, Pam3CSK4, Pam3CAG, CpG, lipidated CpG, phosphorothioated PS-CpG-ODNs or CpG oligodeoxynucleotides (CpG-ODN) such as CpG-A, CpG-B or CpG-C, further preservatives, diluents, emulsifiers, stabilizers, and other components that are known and used in vaccines of the prior art. Moreover, any adjuvant system known in the art can be used in the composition of the present invention. Such adjuvants include, but are not limited to, Freund's incomplete adjuvant, Freund's complete adjuvant, polydispersed β-(1,4) linked acetylated mannan ("Acemannan"), Titermax® (polyoxyethylene-polyoxypropylene copolymer adjuvants from CytRx Corporation), modified lipid adjuvants from Chiron Corporation, saponin derivative adjuvants from Cambridge Biotech, killed *Bordetella pertussis*, the lipopolysaccharide (LPS) of gram-negative bacteria, large polymeric anions such as dextran sulfate, and inorganic gels such as alum, aluminum hydroxide, or aluminum phosphate.

The term "immunogenically effective amount" refers to the amount of antigenic/immunogenic composition which, when administered to a human or animal, elicits an immune response. The effective amount is readily determined by one of skill in the art following routine procedures.

The term "therapeutically effective amount" or "pharmaceutically effective amount" refers to the amount of a construct, particularly an antigenic construct according to the invention and as described herein comprising a modified peptide, particularly a modified antigenic peptide, which, when administered to a human or animal, is sufficient to result in a therapeutic effect in said human or animal. The effective amount is readily determined by one of ordinary skill in the art following routine procedures.

As used herein, the term "critical micellar concentration", also known as CMC, is defined as the concentration of surfactants above which micelles are spontaneously formed. Upon introduction of surfactants (or any surface active materials) into a system the surfactants will initially partition into the interface, thus reducing the systems free energy by a) lowering the energy of the interface (calculated as area× surface tension) and b) by removing the hydrophobic parts of the surfactant from contacts with water. Subsequently, when the surface coverage by the surfactants increases and the surface free energy (surface tension) decreases and the surfactants start aggregating into micelles, thus again decreasing the system's free energy by decreasing the contact area of hydrophobic parts of the surfactant with water. Upon reaching the CMC, any further addition of surfactants will just increase the number of micelles. (IUPAC. Compendium of Chemical Terminology, 2nd ed. Blackwell Scientific Publications, Oxford (1997).)

The phrase "consisting essentially of" is used herein to exclude any elements that would substantially alter the essential properties of the peptides to which the phrase refers. Thus, the description of a peptide "consisting essentially of" excludes any amino acid substitutions, additions, or deletions that would substantially alter the biological activity of that peptide.

Furthermore, one of skill will recognize that, as mentioned above, individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The phrases "isolated" or "biologically pure" refer to material which is substantially or essentially free from components which normally accompany it as found in its native state. Thus, the peptides described herein do not contain materials normally associated with their in situ environment. Typically, the isolated, immunogenic peptides and/or antibodies described herein are at least about 80% pure, usually at least about 90%, and preferably at least about 95% as measured by band intensity on a silver stained gel.

The term "solution", as used herein, relates to a solution being used for preparing the liposomes within the method according to the invention. For example, the solution consists of ethanol, phosphate buffer (PBS), or both. The liposomes are made of dimyristoyl phosphatidyl choline (DMPC), dimyristoyl phosphatidyl ethanolamine (DMPEA), dimyristoyl phosphatidyl glycerol (DMPG) and cholesterol.

Particularly, the liposomes are made of DMPC, DMPG and cholesterol, particularly in a molar ratio of 9.0:1.0:7.0 being mixed, for example, in ethanol. Alternatively, the liposomes are made of dimyristoyl phosphatidyl choline (DMPC), dimyristoyl phosphatidyl ethanolamine (DMPEA), dimyristoyl phosphatidyl glycerol (DMPG) and cholesterol, particularly in a molar ratio of 9.0:1.0:1.0:7.0 molar, respectively, being mixed, for example, in ethanol.

The term "liposome" as used herein is meant to refer to self-assembled spherical structures that contain an inner aqueous compartment surrounded by a lipid bilayer typically composed of phospholipids and sterols. Liposomes are widely used as model systems for cell membrane and as drug carriers in drug delivery systems.

Liposomes that can be used in the compositions of the present invention include those known to one skilled in the art. Any of the standard lipids useful for making liposomes may be used. Standard bilayer and multi-layer liposomes may be used to make compositions of the present invention. While any method of making liposomes known to one skilled in the art may be used, the most preferred liposomes are made according to the method of Alving et al., *Infect. Immun.* 60:2438-2444, 1992, hereby incorporated by reference.

The liposome may have a dual function in that it can be used as a platform for presenting the modified peptide on the liposomal outer surface as described herein in the various embodiments and, at the same time, function as an adjuvant to increase or stimulate the immune response within the target animal or human upon treatment with an antigenic construct according to the invention as described herein in the various embodiments.

Liposomes are composed of (phospho)lipid molecules comprising a hydrophilic head group and a hydrophobic tail. The (phospho)lipid molecules assemble in an aqueous solution such that the hydrophobic parts get oriented toward each other to avoid contact with the aqueous phase, whereas the hydrophilic head groups are oriented such that they make maximal contact with the aqueous surrounding. This leads to spontaneous self-assembly into spherical structures that contain an inner aqueous compartment surrounded by a lipid bilayer.

Liposomes thus contain an outer surface which is oriented towards the aqueous solution surrounding the liposomes and an inner surface lining the inner aqueous compartment.

The term "outer surface" of the liposome as used herein thus is meant to refer to the surface of the liposome which is oriented toward the aqueous phase surrounding the liposomes.

The liposome may contain an adjuvant or an immunomodulator or both. A preferred adjuvant is alum, Pam3CSK4, Pam3CAG, CpG, lipid A, particularly a detoxified lipid A such as, for example, monophosphoryl or diphosphoryl lipid A. Monophosphoryl lipid A (MPLA) may be added at a suitable concentration, particularly at a concentration of between 1 and 10 mg per mmol, more particularly at 5 mg per mmol of phospholipids.

MPLA may be mixed with Octyl-Beta-D-Glucopyranoside (B-OG) and said mixture may be added to the liposome preparation. Alternatively to this step within the method according to the invention, the adjuvant may be incorporated together with the other lipids (DMPC; DMPG and Cholesterol) in a solution such as ethanol.

As used herein, the term "soluble" or "solubilized" means partially or completely dissolved in an aqueous solution. Particularly, within the method of the invention, the modified peptide may be solubilized in the presence of surfactant such as B-OG, PBS or mixture thereof. The particular solubilization conditions depend on different parameters such as pH, buffer, surfactant, concentration and temperature.

The terms "detecting" or "detected" as used herein mean using known techniques for detection of biologic molecules such as immunochemical or histological methods and refer to qualitatively or quantitatively determining the presence or concentration of the biomolecule under investigation.

The terms "antibody", "antibodies" or "functional parts thereof" as used herein is an art recognized term and is understood to refer to molecules or active fragments of molecules that bind to known antigens, particularly to immunoglobulin molecules and to immunologically active portions of immunoglobulin molecules, i.e molecules that contain a binding site that immunospecifically binds an antigen. The immunoglobulin according to the invention can be of any type (IgG, IgM, IgD, IgE, IgA and IgY) or class (IgG1, IgG2, IgG3, IgG4, IgA1 and IgA2) or subclasses of immunoglobulin molecule.

"Antibodies" are intended within the scope of the present invention to include monoclonal antibodies, polyclonal, chimeric, single chain, bispecific, simianized, human and humanized antibodies as well as active fragments thereof. Examples of active fragments of molecules that bind to known antigens include Fab and F(ab')2 fragments, including the products of a Fab immunoglobulin expression library and epitope-binding fragments of any one of the antibodies and fragments mentioned above.

These active fragments can be derived from an antibody of the present invention by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

A "humanized antibody" refers to a type of engineered antibody having its CDRs derived from a non-human donor immunoglobulin, the remaining immunoglobulin-derived parts of the molecule being derived from one (or more) human immunoglobulin(s).

A humanized antibody may further refer to an antibody having a variable region where one or more of its framework regions have human or primate amino acids. In addition, framework support residues may be altered to preserve binding affinity. Methods to obtain "humanized antibodies" are well known to those skilled in the art. (see, e.g., Queen et al., Proc. Natl Acad Sci USA, 86:10029-10032 (1989), Hodgson et al., Bio/Technoloy, 9:421 (1991)).

A "humanized antibody" may also be obtained by a novel genetic engineering approach that enables production of affinity-matured humanlike polyclonal antibodies in large animals such as, for example, rabbits (http://www.rctech-.com/bioventures/therapeutic.php).

The term "monoclonal antibody" is also well recognized in the art and refers to an antibody that is mass produced in the laboratory from a single clone and that recognizes only one antigen. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces large quantities of the antibody.

The term "antigen" refers to an entity or fragment thereof which can induce an immune response in an organism, particularly an animal, more particularly a mammal including a human. The term includes immunogens and regions responsible for antigenicity or antigenic determinants.

Also as used herein, the term "immunogenic" refers to substances which elicit or enhance the production of antibodies, T-cells and other reactive immune cells directed against an immunogenic agent and contribute to an immune response in humans or animals.

An immune response occurs when an individual produces sufficient antibodies, T-cells and other reactive immune cells against administered immunogenic compositions of the present invention to moderate or alleviate the disorder to be treated.

The term "hybridoma" or "hybridoma cell" is art recognized and is understood by those of ordinary skill in the art to refer to a cell produced by the fusion of an antibody-producing cell and an immortal cell, e.g. a multiple myeloma cell. This hybrid cell is capable of producing a continuous supply of antibody. See the definition of "monoclonal antibody" above for a more detailed description of the method of fusion.

In another specific embodiment of the invention a modified antigenic peptide according to the invention and as described herein before in the various embodiments is provided covalently bound to an anchor-type molecule which is capable of inserting into the carrier/adjuvant thereby fixing the peptide to the carrier/adjuvant and presenting it on or in close proximity to the surface of a carrier/adjuvant molecule such that hydrophobic interactions can become effective as described herein in the various embodiments before.

As used herein, the term "disease or disorder" relates basically to any disease that can be treated by a liposome-based construct according to the present invention and as described herein in the various embodiments.

In particular the term "disease or disorder" relates a proteopathy, a disease involving protein misfolding and/or a disease involving protein accumulation or aggregation" such as, for example, a disease or disorder which may be selected from the group consisting of AA amyloidosis, AH (heavy chain) amyloidosis, AL (light chain) amyloidosis, Alexander disease, Alzheimer's disease, amyotrophic lateral sclerosis, aortic medial amyloidosis, apoA1 amyloidosis, apoA2 amyloidosis, apoA4 amyloidosis, aortic medial amyloidosis, CADASIL, cardiac atrial amyloidosis, cataract, cerebral amyloid angiopathy, corneal lactoferrin amyloidosis, critical illness myopathy, cutaneous lichen amyloidosis, cystic fibrosis, dialysis amyloidosis, Familial amyloidotic neuropathy, familial British dementia, familial Danish dementia, familial visceral amyloidosis, fibrinogen amyloidosis, Finnish hereditary amyloidosis, frontotemporal lobar dementia, Glaucoma, hereditary cerebral hemorrhage with amyloidosis—Dutch type, hereditary cerebral hemorrhage with amyloidosis—Icelandic type, Huntington's disease and other triplet disorders, hereditary lattice corneal dystrophy, inclusion body myositis/myopathy, lysozyme amyloidosis, Mallory bodies, medullary thyroid carcinoma, Odontogenic (Pindborg) tumor amyloid, Parkinson's disease, pituitary prolactinoma, primary systemic amyloidosis, primary cutaneous amyloidosis, prion disease, pulmonary alveolar proteinosis, retinal ganglion cell degeneration in glaucoma, prion disease, seminal vesicle amyloid, seipinopathy, senile systemic amyloidosis, serpinopathy, sickle cell disease, synucleinopathy, tauopathy, and type 2 diabetes, fungal infections (e.g. mycose, candidiase, tinea, leishmaniose), or inflammation, in an animal or human patient in need of such a treatment The term "disease or disorder" further relates to cell proliferative diseases and disorders including multiple myeloma and other cancers such as colorectal carcinoma, melanoma; IL-2, cancers, especially breast cancer, lung cancer, liver cancer, stomach and spleen cancers, and tumors; IL-4, cancer; TNF, cancer; IGF-1 antisense, brain tumors; IFN, neuroblastoma; GM-CSF, renal cell carcinoma; MDR-1, cancer, especially advanced cancer, breast and ovarian cancers; and HSV thymidine kinase, brain tumors, head and neck tumors, mesothelioma, ovarian cancer, leukemia. The term "disease or disorder" also relates to fungal infections such as mycoses, candidiases, tinea, and leishmaniose.

BRIEF DESCRIPTION OF THE DRAWINGS AND TABLES

FIG. 1 shows a flow chart of L16 process.

FIG. 2 shows analysis of anti-TAU5-20 [pY18] IgG antibodies in the plasma of C5BL/6 mice after receiving ACI-33 vaccines, either manufactured with thin film method (Process A) or with process L15. A pre-bleeding was done at −7 days followed by day 7, 21 and 35 after the first immunization. Results are expressed as mean±standard deviation obtained in groups of 10 mice.

FIG. 3 shows analysis of anti-TAU396-408 [pS396/pS404] IgG antibodies in the plasma of C5BL/6 mice after receiving ACI-35 vaccines, either manufactured with thin film method (Process A) or with process L15. A pre-bleeding was done at −7 days followed by day 7, 21 and 35 after the first immunization. Results are expressed as mean±standard deviation obtained in groups of 10 mice.

FIG. 4 shows analysis of anti-Aβ IgG antibodies in the plasma of C5BL/6 mice after receiving PaI 1-15 vaccines, either manufactured with process D (ACI-24 process D#2) or with process L15. A pre-bleeding was done at −7 days followed by day 7, 21 and 35 after the first immunization. Results are expressed as mean±standard deviation obtained in groups of 10 mice.

FIG. 5 shows analysis of anti-Aβ IgG antibodies in the plasma of C5BL/6 mice after receiving PaI 1-15 vaccines, either manufactured with the process D (ACI-24 process D#1) with the process L15 (ACI-24 process L15 A; L15B and L15C) or with the ACI-24 process L16. A pre-bleeding was done at −7 days followed by day 7, 21 and 35 after the first immunization. Results are expressed as mean±standard deviation obtained in groups of 10 mice.

FIG. 6a shows analysis of the anti-T8 IgG antibody titers in the plasma of C5BL/6 mice after receiving ACI-41 (peptides T8 and T9) vaccines manufactured with L15 process. A pre-bleeding was done at −7 days followed by day 7, 21 and 35 after the first immunization. Results are expressed as mean±standard deviation obtained in groups of 10 mice.

FIG. 6b shows analysis of the anti-T9 IgG antibody titers in the plasma of C5BL/6 mice after receiving ACI-41 (peptides T8 and T9) vaccines manufactured with L15 process. A pre-bleeding was done at −7 days followed by day 7, 21 and 35 after the first immunization. Results are expressed as mean±standard deviation obtained in groups of 10 mice.

Table 1 to 3 describe batches of L15 process producing PaI 1-15 vaccine. The batches were generated in order to evaluate the physicochemical and in-vivo reproducibility of ACI-24 vaccine generated with process L15: ACI-24-100316-A; ACI-24-100316-B and ACI-24-100316-C. The three vaccines were generated independently.

Table 4 describes a batch of L16 process with normal MPLA concentration producing PaI 1-15 vaccine. The batch was manufactured with process L16 (antigen and adjuvant added after liposome formation)—ACI-24-091127-A.

Table 5 describes a batch of L16 process with high MPLA concentration producing PaI 1-15 vaccine. The batch was manufactured with process L16 (antigen and adjuvant added after liposome formation)—ACI-24-091127-B.

Table 6 describes a batch of L15 process producing T1 vaccine ACI-33-091127.

Table 7 describes a batch of thin film process producing T1 vaccine—ACI-33-091808-A.

Table 8 describes a batch of L15 process producing T3 vaccine—ACI-35-091127.

Table 9 describes a batch of thin film process producing T3 vaccine—ACI-35-0910820-A.

Table 10 describes a batch of L15 process producing T8/T9 vaccines—ACI-41-100531.

Table 11 and 12 describe two independent batches generated by the cross flow ethanol injection method (process D) for producing PaI 1-15 vaccine—ACI-24 process D#1 and D#2, respectively.

Table 13 shows absorbance values for triplicate analyses of ACI-24-100316-A using the BCA assay.

Table 14 shows summary of analyses results of different ACI-24 processes and batches.

The foregoing description will be more fully understood with reference to the following Examples. Such Examples, are, however, exemplary of methods of practicing the present invention and are not intended to limit the scope of the invention.

The following Examples illustrate the invention.

EXAMPLES

Example 1: Preparation of a Liposome-Based Antigenic Construct (Process L15; L16 and L20)

1.1. Process L16

Figure 1:
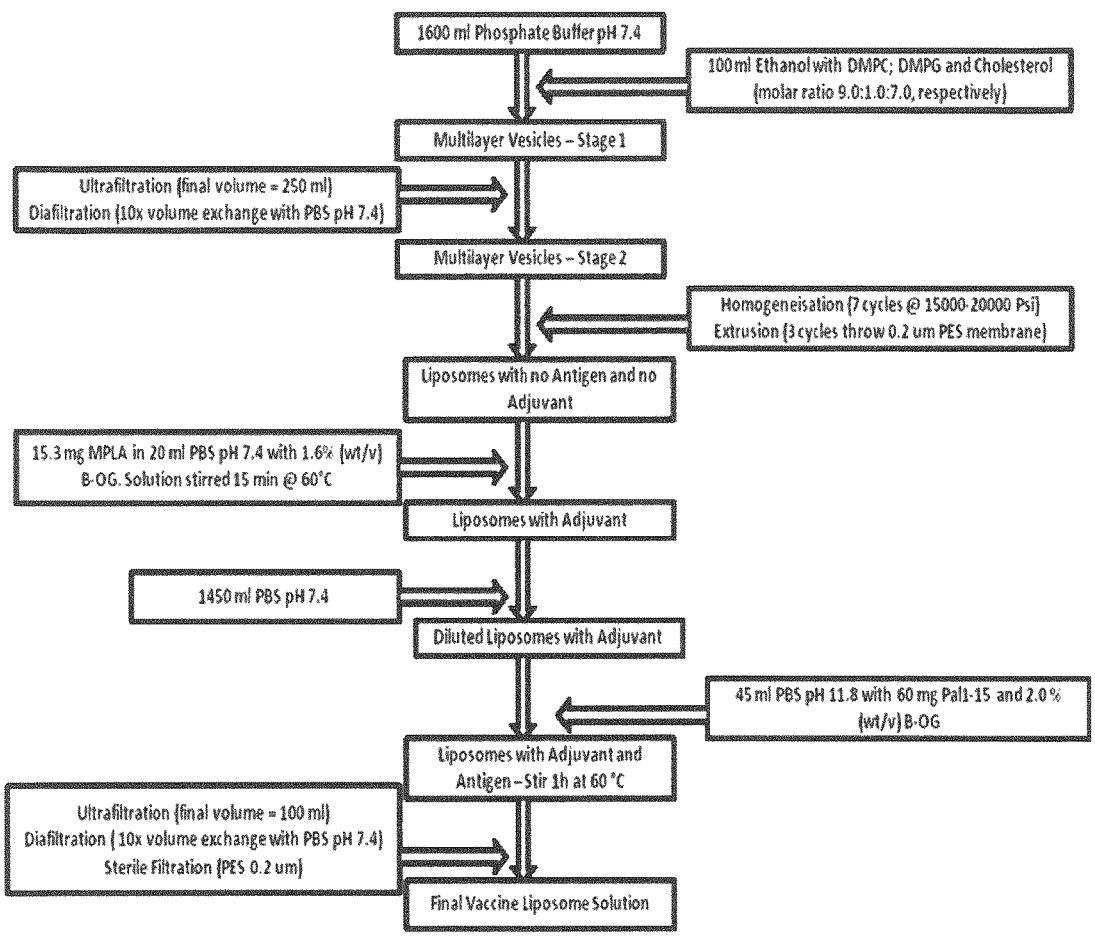

1.1.1 Liposome Preparation:

The phospholipids dimyristoylphosphatidylcholine (DMPC), dimyristoylphosphatidyl-glycerol (DMPG) and cholesterol (Avanti Polar Lipids. Alabaster, Ala.) were mixed in ethanol (100 ml) at a molar ratio of 9.0; 1.0 and 7.0, respectively. A perfectly clear solution was formed following a continuous agitation at 60° C. for 15 min (see FIG. 1). This lipid mixture was then diluted (17×) by injecting the solution (100 ml) in 1600 ml phosphate buffer (PBS) pH 7.4, allowing the formation of multi-layer vesicles (Multilayer Vesicles—stage 1). The resulting preparation was then concentrated by ultrafiltration (Vivaflow 200-100.000 MWCO Polyethersulphone with a flow of 200 ml/min) and the reaction volume was reduced from 1700 ml to 250 ml (Ultrafiltration step). The concentrated solution was further submitted to dialysis in a Vivaflow 200 device where a 10× volume exchange is performed with PBS pH 7.4 (Diafiltration step). The dialysed solution (Multilayer vesicles—stage 2) was then homogenized (7 cycles at 15.000-20.000 Psi) in an Emulsiflex C5 device from Avestin (Homogenization step), followed by 3 cycles of Extrusion (using the same Emulsiflex instrument) through a 0.2 um Polycarbonate membrane with a diameter of 47 mm (Extrusion step). Following those last two sizing steps, unilamelar liposomes with no antigen and adjuvant were formed (Empty liposome preparation).

1.1.2 Preparation of Adjuvant Solution:

A 765 ug/ml solution of MPLA was prepared in 20 ml PBS pH 7.4 with 1.6% (wt/v) Octyl-Beta-D-Glucopyranoside (B-OG). The resulting solution contained detergent (B-OG) at a concentration above its critical micellar concentration (CMC) of 0.73% (wt/v). This solution was then heated at 60° C. for 30 min and manually injected into the 250 ml preparation of empty liposomes. During this dilution step, the detergent concentration is diluted down 13.5×, resulting in a final concentration of 0.12% (wt/v), a concentration of B-OG below its CMC ($1^{st}$ dilution step). The Liposome solution containing the adjuvant (MPLA) is then diluted (7×) by injecting 1450 ml of PBS pH 7.4 ($2^{nd}$ dilution step).

1.1.3 Preparation of Peptide Solution:

1.33 mg/ml of the peptide Aβ-PaI 1-15 was prepared in PBS pH 11.8 (total volume 45 ml) with 2.0% (wt/v) B-OG. The resulting solution comprised a detergent concentration above its critical micellar concentration (CMC) of 0.73% (wt/v). This solution was stirred heated at 60° C. and stirred for 15 min, until a clear solution was formed. The peptide solution (45 ml) was then added to the solution of liposome with adjuvant (1700 ml) and stirred for 1 h at 60° C. resulting in a solution having a final B-OG concentration of (0.05%), which is far below the detergent's CMC (0.73%) (Dilution step). The resulting solution was then concentrated by ultrafiltration (same condition mentioned above) and the final vaccine volume set to 100 ml. The concentrated solution was dialysed by diafiltration, where a 10× volume exchange was performed with PBS pH 7.4.

In a final step, the vaccine solution was sterile filtered through a 0.2 um Polyethersulfone membrane filter (Sartorius 16541-K). Each filter was used to sterile filter 5 ml of vaccine solution into 15 ml Falcon tubes. This last process step is executed in a sterile environment (laminar flow hood).

1.2. Process L15

Process L15 only differs from process L16 in that the adjuvant (e.g. MPLA) is added together with the lipids in the ethanol solution prior to liposome formation and sizing steps. Therefore, the process of adding adjuvant following liposome formation is suppressed.

1.3. Process L20

1.3.1 Liposome Preparation:

The phospholipids dimyristoylphosphatidylcholine (DMPC), dimyristoylphosphatidyl-glycerol (DMPG) and cholesterol (Avanti Polar Lipids. Alabaster, Ala.) were mixed in ethanol (8.55 ml) at a molar ratio of 9.0; 1.0 and 7.0, respectively. A perfectly clear solution was formed following a continuous agitation at 60° C. for 15 min. MPLA (7.5 mg) was solubilized in 0.45 ml tert-butanol at 60° C. and added to the ethanol solution. This lipid mixture was then diluted (10×) by injecting the solution (9.0 ml) in 90 ml phosphate buffer (PBS) pH 7.4, allowing the formation of multi-layer vesicles. The resulting preparation was then extruded through a pack of 3 polycarbonate membranes with a pore size of 0.08 um using an Emulsiflex C5 device from Avestin or a Lipex Extruder from Northern Lipids and diluted with PBS pH 7.4 to a final volume of 425 ml.

1.3.2 Preparation of Peptide Solution:

1.33 mg/ml of the TAU peptide T3 was prepared in PBS pH 11.8 (total volume 22.5 ml) with 5.0% (wt/v) B-OG. The resulting solution comprised a detergent concentration above its critical micellar concentration (CMC) of 0.73% (wt/v). This solution was stirred heated at 60° C. and stirred for 15 min, until a clear solution was formed. The peptide solution (22.5 ml) was then added to the solution of liposome with adjuvant (425 ml) and stirred for 30 min at 60° C. resulting in a solution having a final B-OG concentration of (0.20%), which is far below the detergent's CMC (0.73%) (Dilution step). The resulting solution was then concentrated by ultrafiltration (same condition mentioned above) and the final vaccine volume set to 50 ml. The concentrated solution was dialysed by diafiltration, where a 10× volume exchange was performed with PBS pH 7.4.

In a final step, the vaccine solution was sterile filtered through a 0.2 um Acetate cellulose filter (Minisart 16534). Each filter was used to sterile filter 5 ml of vaccine solution into 15 ml Falcon tubes. This last process step is executed in a sterile environment (laminar flow hood).

Scalability of process L20 has been demonstrated by generating batches with different volumes (50 and 150 ml) and with identical biophysical and immunological properties.

1.4 Results

Table 4 describes a batch of L16 process with normal MPLA concentration producing PaI 1-15 vaccine (ACI-24-091127-A). The batch was manufactured with process L16 (antigen and adjuvant added after liposome formation) as described in Example 1—ACI-24-091127-A. Normal MPLA concentration means an identical MPLA incorporation as adopted for the process L15 described in the paragraph above.

Table 5 describes a batch of L16 process with high MPLA concentration producing PaI 1-15 vaccine (ACI-24-091127-B). The batch was manufactured with process L16 (antigen and adjuvant added after liposome formation) as described in Example 1. High MPLA concentration means a MPLA load in the final vaccine formulation which is approximately 8 times higher than in the process L15 Such high MPLA yield is not obtainable with the cross-flow ethanol injection method (process D)

The advantages of the L16/L15 processes for producing PaI 1-15 vaccine are evident when comparing the outcome of process D for producing PaI 1-15 vaccine (see Table 1 to 3, 11 and 12, respectively). As we can see in the tables, MPLA hydrolysis (reported by formation of congener B) was significantly reduced in process L15/L16 as compared to process D. Moreover, peptide distribution with process L15/L16 reported an increase of antigen exposure towards the outer aqueous surface as compared to process D (Table 14).

Figure 13:
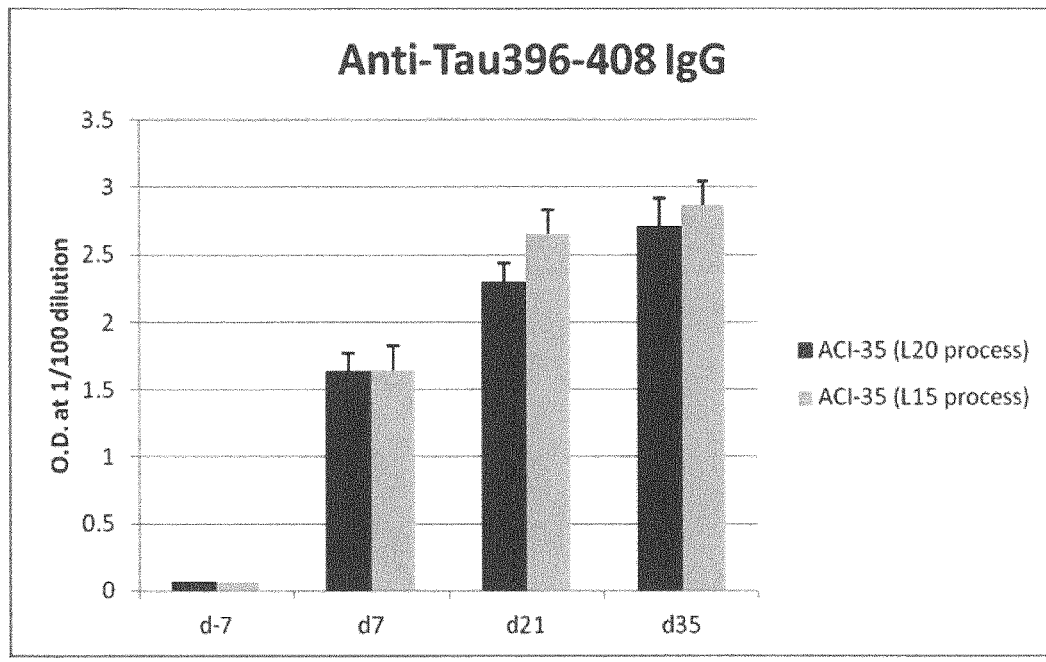
FIG. 13 shows IgG titers at day −7; 7; 21 and 35 after immunization with ACI-35 vaccine generated with either process L15 or L20.

FIG. 13 shows the IgG titers of mice immunized with a Tau vaccine generated either with process L15 or L20. As can be observed, identical titer yields are obtained for the two processes.

Scalability of process L20 has been demonstrated by generating batches with different volumes (50 and 150 ml) and with identical biophysical and immunological properties.

Figure 2:
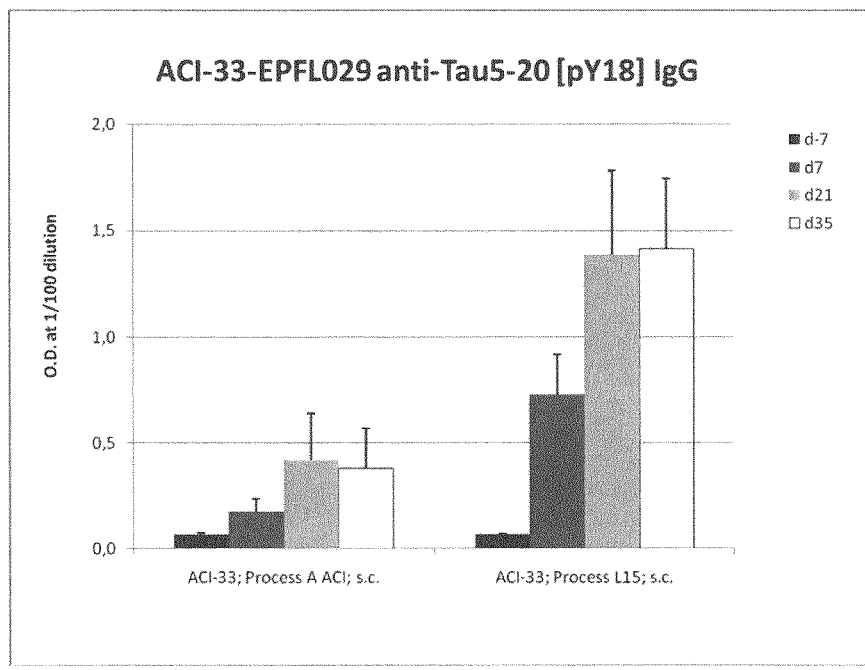

All processes that I have worked are theoretically stable, though we only have data for the L20 process Example 2: Comparison of L15 Method Vs Thin Film Method Producing ACI-33 Vaccine Table 6 and 7 describe a batch of L15 process and thin film process (process A as described in WO2007/068411), respectively, for producing ACI-33 vaccines. In FIG. 2, the anti-Tau5-20 [pY18] IgG antibody titers in the plasma of C5BL/6 mice after receiving ACI-33 vaccines are shown, either manufactured with the thin film method (Process A) or with the process L15. Mice challenged with ACI-33 vaccines manufactured with process L15 gave higher antibody titers than mice challenged with a process A vaccine. This effect should be attributed to the L15 vaccine properties which not only display a higher peptide load with an exclusive peptide distribution but also to the fact that L15 process generates smaller liposomes (<200 nm) than those made by the thin-film method.

Figure 3:
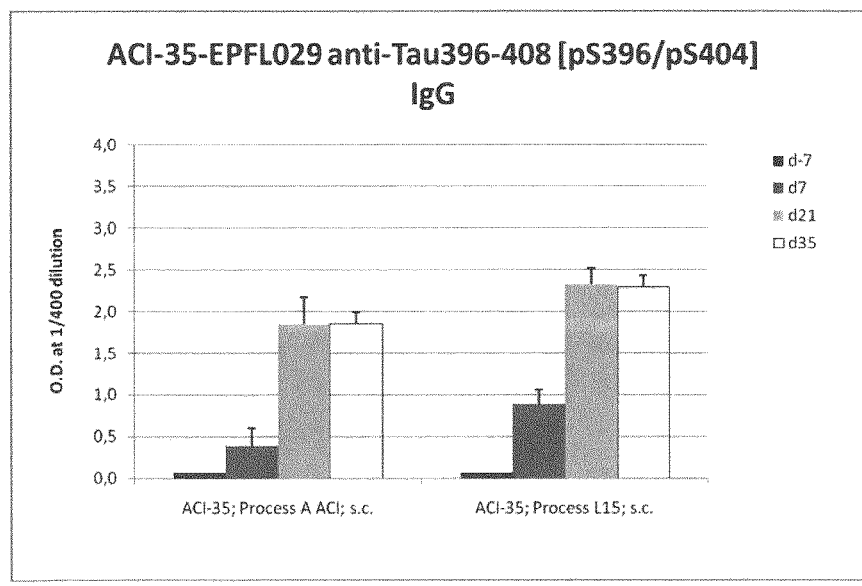

Example 3: Comparison of L15 Method Vs Thin Film Method Producing ACI-35 Vaccine Table 8 and 9 describe a batch of L15 process and thin film process (process A as described in WO2007/068411), respectively, for producing ACI-35 vaccine. In FIG. 3 the anti-TAU396-408 [pS396/pS404] IgG antibody titers in the plasma of C5BL/6 mice after receiving ACI-35 vaccines are shown, either manufactured with the thin film method or with the process L15. Mice challenged with ACI-35 vaccine manufactured by process L15 gave higher antibody titers than mice challenged with a process A vaccine. This effect should be attributed to the L15 vaccine properties which not only allow a higher peptide load with an exclusive peptide distribution but also to the fact that L15 process generates smaller liposomes (<200 nm) than the thin-film method.

Figure 4:
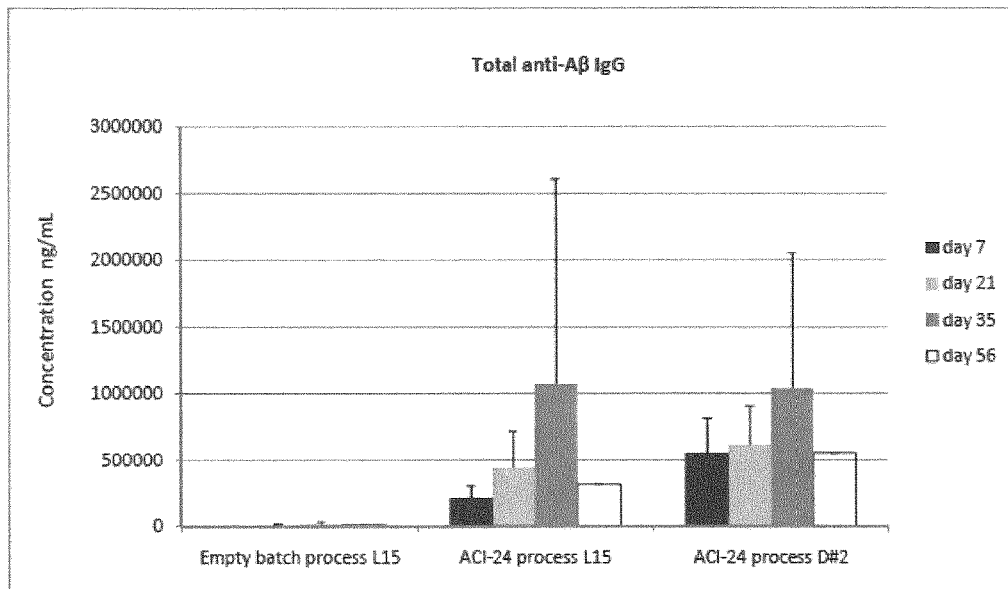

Example 4: Comparison of L15 Method Vs Cross Flow Ethanol Injection (Process D) Method Producing T1 Vaccine FIG. 4 shows the anti-Aβ IgG antibody titers in the plasma of C5BL/6 mice after receiving PaI 1-15 vaccines, either manufactured with the process D (ACI-24 process D #2) or with the process L15. Results highlight identical antibody titers for the two vaccines. However, L15 process only contains negligible amounts of MPLA hydrolysis products (e.g. MPLA congener B) as compared to the other method (process D) where MPLA hydrolysis occurs to a much vast extent in a non-controlled fashion. The immunogenicity of different MPLA congeners (e.g. congener A which corresponds to its non hydrolyzed form and congener B, which is one of congener A hydrolyzate products) are not know. A process which does not contain the MPLA hydrolysis products has the advantage of a high batch reproducibility and the vaccines produced by such a process show improved quality and stability.

Example 5: In-Vivo Comparison of Method L15 Vs L16 and Immune Reproducibility of Process L15

Figure 5:
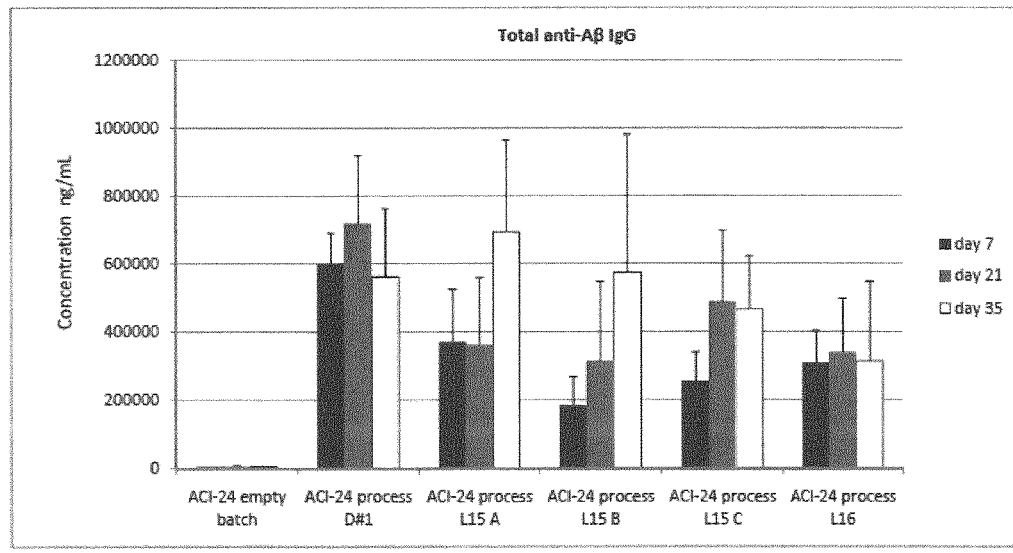

FIG. 5 shows the anti-Aβ IgG antibody titers in the plasma of C5BL/6 mice after receiving PaI 1-15 vaccines, either manufactured with the process D (ACI-24 process D #1), with the 3 independently generated L15 vaccines and one vaccine generated with the L16 process. Results show identical antibody titers for the 3 individual L15 vaccines highlighting in-vivo immunological reproducibility. At day 35 after immunization there were no major differences in the antibody titers between L15 vaccine and process D vaccine. However, MPLA was hydrolyzed to a much greater extent in the ethanol cross-flow injection method (process D) than compared to the L15 or L16 processes.

The antibody titers obtained with the L16 process are slightly lower at day 35 when compared to L15 batches. This result may be due to an excess of MPLA on the external phospholipid bilayer as compared to the process L15. Different doses of MPLA should be tested on both methods in order to obtain a clearer response on effect of adjuvant concentration on the immune response. However, the fact that MPLA can be added after liposome formation offers the advantage of incorporating the adjuvant only when needed into stocked empty-liposomes. This approach may prevent MPLA hydrolysis during storage in a liposome formulation.

Example 6: In-Vivo Generation of Two Different Antibodies by Generating Liposomes with the L15 Process Containing Two Antigens (T8 and T9 Antigen on ACI-41 Vaccine)

Figure 6A:
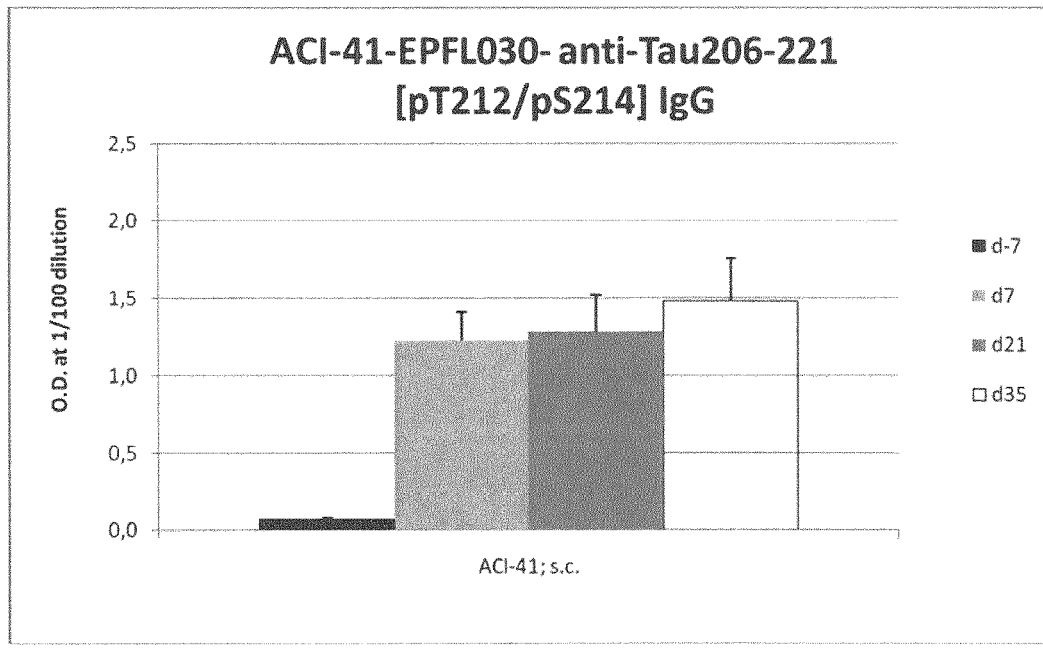
Figure 6B:
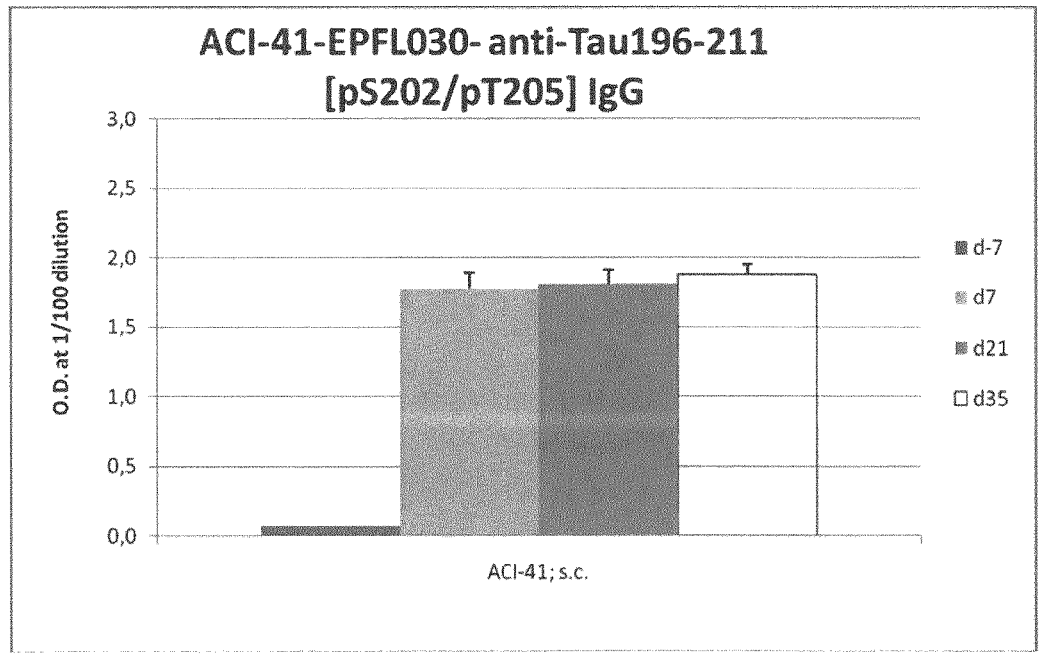

Table 10 describes a batch of L15 process for producing a vaccine containing a mixture of T8 and T9 peptide sequences. The differences in T8 and T9 peptide solubility and purity may affect the final antigen yield in the vaccine formulation. In FIGS. 6a and 6b it is shown that ACI-41 vaccine (containing two different antigens—T8 and T9) can induce a specific antibody response for the two epitopes present on the same liposomes.

Example 7: In-Vivo Generation of Antibodies by Generating Liposomes with the L15 Process Containing Different Adjuvants than MPLA: Lipidated CpG Adjuvant (Vaccine ACI-17) or Pam2CSK4 (Vaccine ACI-18)

Vaccines ACI-17 and ACI-18 manufactured by process L15 were prepared as previously described in Example 1.2 with the only difference in adjuvant selection. Adjuvants used in vaccines ACI-17 and ACI-18 were lipidated CpG and Pam2CSK4, respectively.

Figure 14:
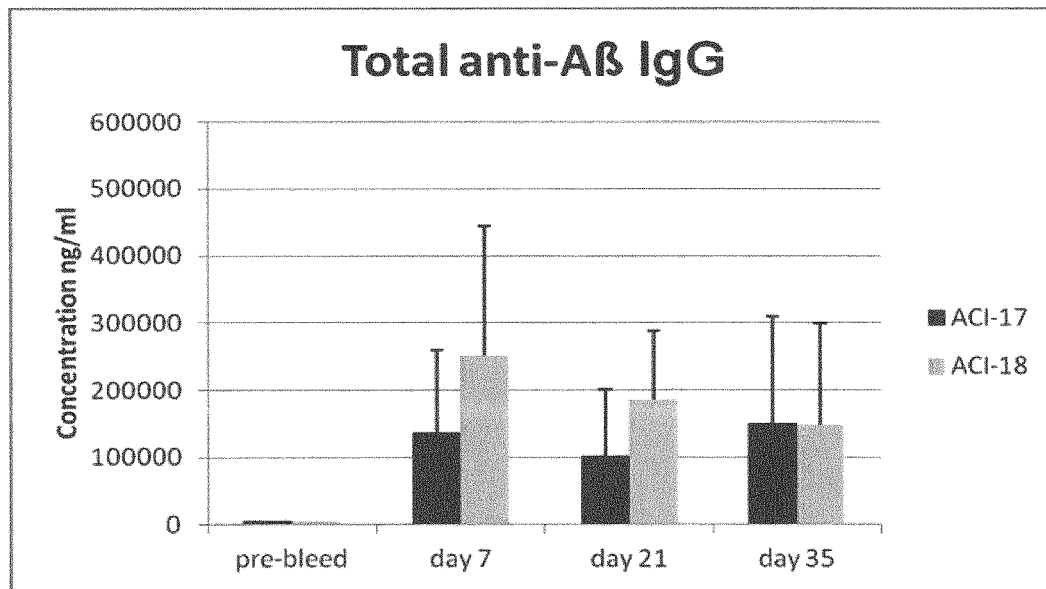
FIG. 14 shows total anti-Aβ titers obtained after 7, 21 or 35 days after injecting either vaccine ACI-17 (process L15 where MPLA is replaced by lipidated CpG adjuvant) or vaccine ACI-18 (process L15 where MPLA is replaced by Pam2CSK4 adjuvant) in mice.

FIG. 14 shows the anti-Aβ IgG antibody titers in the plasma of C5BL/6 mice after receiving PaI 1-15 vaccines, manufactured with the process L15 where MPLA is replaced by lipidated CpG adjuvant (vaccine ACI-17) or by Pam2CSK4 (vaccine ACI-18). Results highlight the technology flexibility in loading the liposomes with adjuvants different from MPLA and still inducing an immune response which generates antibodies which bind to Aβ.

Example 8: Determination of the Membrane Topology of PaI1-15 in ACI-24 Using a BCA Colorimetric Assay The Bicinchoninic acid protein quantification assay (BCA) was developed and tested for linearity, specificity and precision. Finally the assay was implemented to analyse the peptide topology in different batches of ACI-24 prepared by different processes. The BCA assay is based upon a two-step reaction in which Copper(II) is firstly reduced to Copper(I) in the presence of peptide under basic conditions (Biuret reaction). In a second step, Copper(I) chelates with the reagent Bicinchoninic acid to generate a purple colored complex that can be measured by Absorbance and which is proportional to the peptide content. Due to the charge of Copper(II) and Bicinchoninic acid, these reagents would not be expected to cross the liposome bilayer and so should quantify only peptide on the outer membrane. To quantify the total peptide content, the liposomes can be lysed in the presence of a detergent and then the quantification performed using the BCA reagent. The proportion of PaI1-15 on the outer surface can then be determined from the ratio of peptide on the outer surface and total peptide. As a control for specificity, liposomes lacking peptide (empty liposomes) were used. Likewise, in order to ensure that peptide on the outer surface could be quantified and that the bicinchoninic acid and copper would not traverse the liposome membrane, a control batch composed of a water soluble peptide Ac1-15 fully encapsulated within the interior of liposomes was tested.

The standard BCA assay conditions were modified in order to optimize the signal/noise ratio as well as the reaction specificity. The parameters that were optimized include i) concentration of bicinchoninic acid and copper (II), ii) concentration of ACI-24, iii) reaction temperature and iv) reaction time (data not shown).

8.1 Peptide on Outer Liposome Surface

Liposomes were diluted 2-fold with PBS and 240 µL added to a 96-well flat-bottom transparent plate. 60 µL of 4× concentrated BCA reagent (micro-BCA Protein Assay Kit, 1.88 mL reagent A, 1.80 mL reagent B, 256 µL reagent C) was added and the samples mixed and left at RT in the absence of light for 90 min.

8.2 Total Peptide Content

In order to lyse liposomes to quantitate total peptide content, liposomes were diluted 2-fold with SDS to give a final SDS concentration of 2.25% (v/v). 300 µL of liposomes in SDS was then heated in a sealed plastic eppendorf at 70° C. for 2 h and then cooled to RT over 2 h. The efficiency of lysing could be followed by monitoring the Absorbance in the range 320-600 nm. 240 µL of this transparent solution was then added to a 96-well flat-bottom transparent plate. 60 µL of 4× concentrated BCA reagent was added and the sample mixed and left at RT in the absence of light for 90 min.

8.3 Absorbance Analysis

Absorbance measurements were performed over the range 410-700 nm and the Abs at 562 nm was used to calculate the proportion of peptide on the outer liposome surface. Since liposomes scatter light due to their large size, this background absorbance is corrected by subtraction from the absorbance of liposomes measured with the BCA assay according to the following formula:

% peptide on outer membrane=(Abs liposomes+BCA)−(Abs liposomes)/(Abs lysed liposomes+BCA)−(Abs lysed liposomes)

8.4 Results
8.4.1 Linearity

Figure 7:
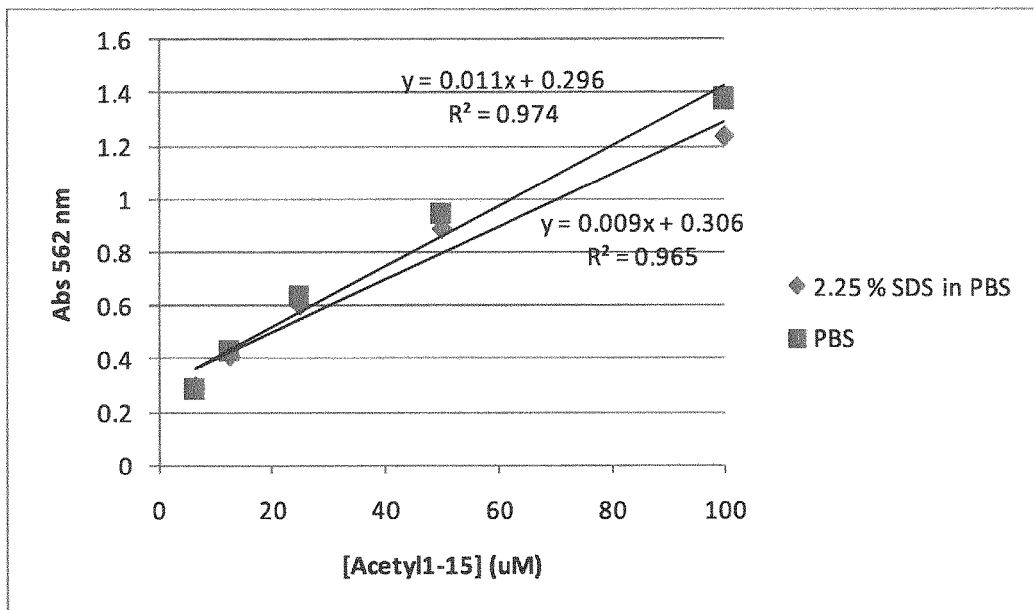
FIG. 7 shows bicinchoninic acid protein quantification assay (BCA) standard curve of Ac1-15 peptide after solubilizing in either PBS or 2.25% SDS.

To determine the linear range of the assay, standards of the water soluble peptide Ac1-15 (Polypeptides, France) was analyzed, upon solubilzation in PBS, with the BCA assay in the range 6.25→100 µM final peptide concentration. Good linearity was found over this range ($R^2 > 0.97$) (FIG. 7). ACI-24 samples are analyzed at 2-fold dilution which means a theoretical peptide concentration of 60 µM which is thus well within the linear range of the assay.

8.4.2 Specificity
8.4.2.1 Effect of SDS:

In order to ensure that the presence of 2.25% SDS detergent would not interfere with the assay, standards of Ac1-15 peptide were prepared in SDS as for liposome samples. As can be seen in FIG. 7, Ac1-15 solubilized in SDS gave a similar standard curve compared with that solubilized in PBS.

Figure 8:
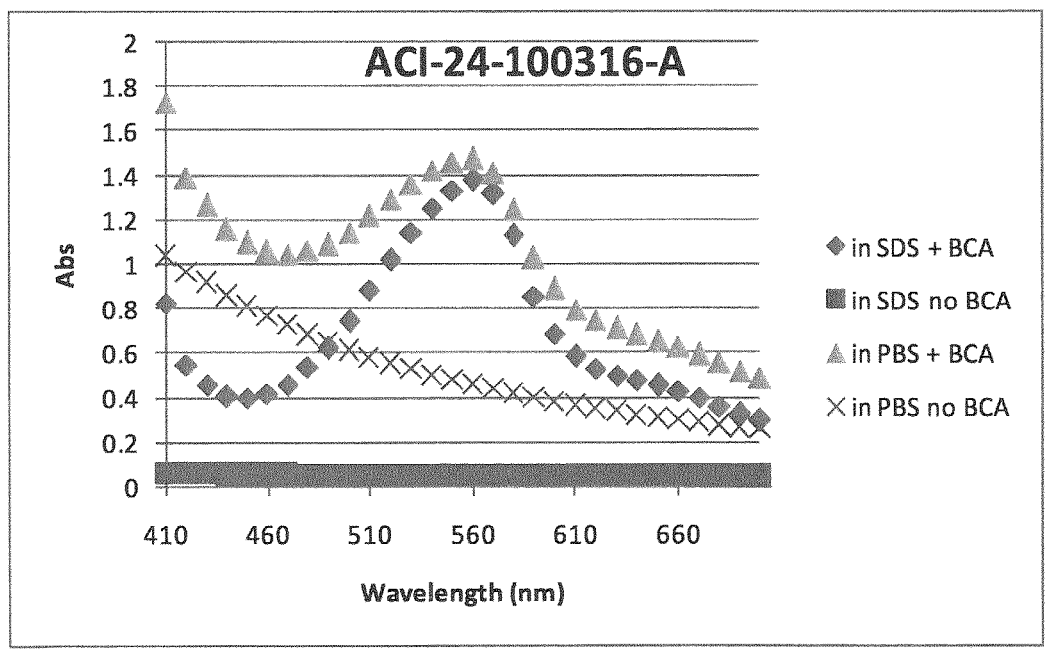
FIG. 8 shows Absorbance spectra of ACI-24 with or without BCA reagents, in the presence of either PBS or SDS.
Figure 9:
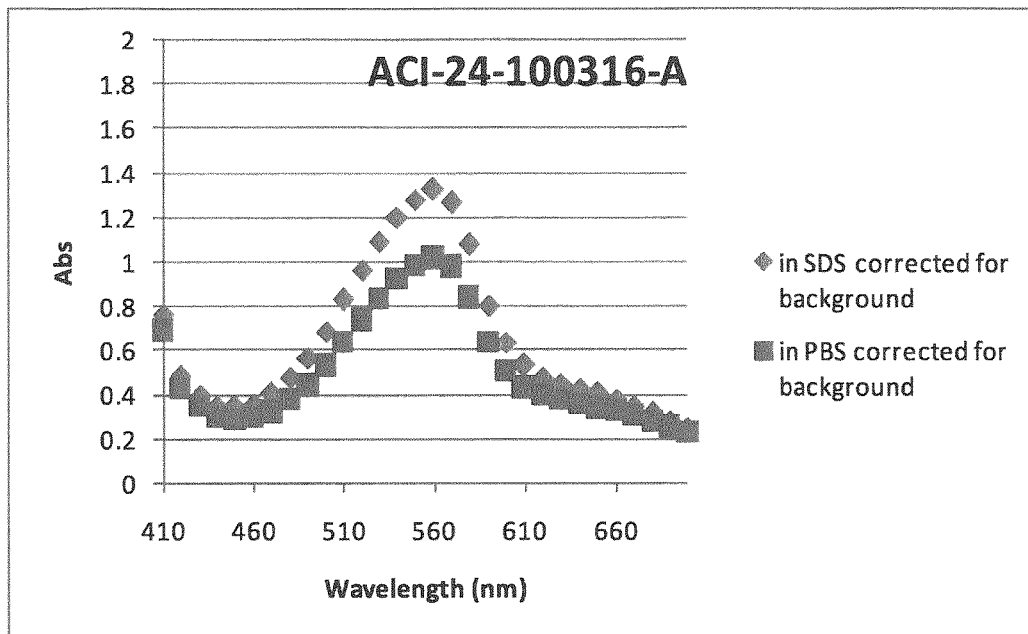
FIG. 9 shows comparison of ACI-24 absorbance spectra upon treatment with BCA reagents and correction for intrinsic liposome absorbance.

8.4.2.2 Effect of ACI-24 Liposome Samples:

Absorbance spectra of an ACI-24 batch (process L15) are shown in FIG. 8. Strong absorbance is seen at 562 nm characteristic of the BCA-Cu(I) complex, both for ACI-24 treated with BCA reagents either in the presence of PBS or SDS. No peaks were observed for liposomes in PBS or SDS without treatment with BCA reagents. As expected, liposomes in PBS alone give rise to background absorbance at 562 nm whereas liposomes lysed with SDS to give micelles show only minor absorbance over the range 410→700 nm. When the background absorbance is corrected, the absorbance spectra of ACI-24 in PBS or SDS are similar but differ only in signal intensity at close to 562 nm (FIG. 9).

Figure 10:
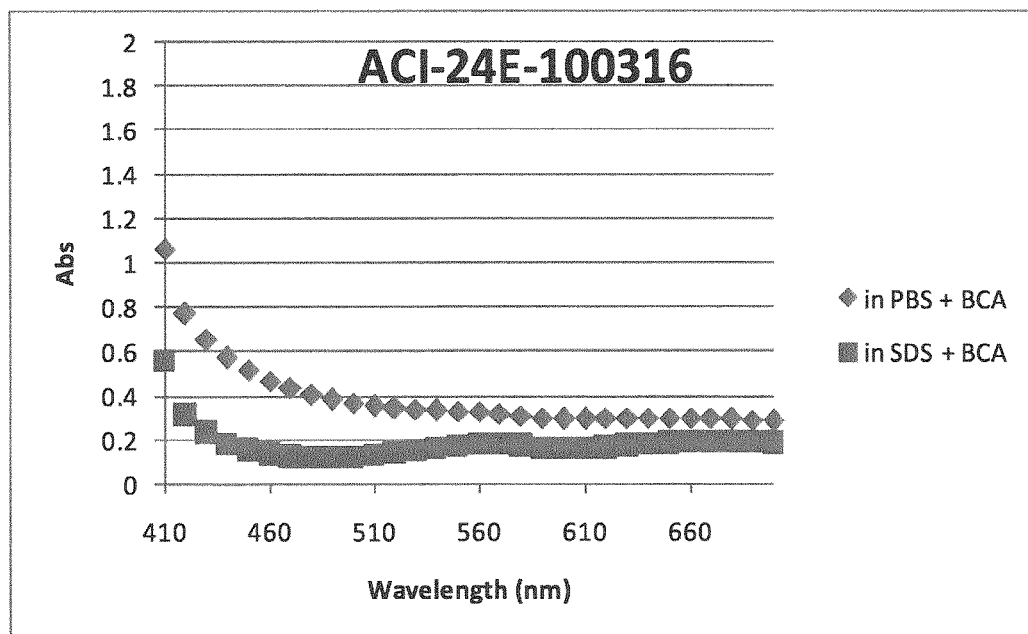
FIG. 10 shows absorbance spectra of liposomes lacking peptide (empty liposomes, ACI-24E).

8.4.2.3 Effect of Liposome Matrix:

In order to determine whether the Liposome matrix could interfere with the BCA assay, a batch of liposomes identical to ACI-24 but lacking peptide (ACI-24E-100316) was analyzed. As can be seen in FIG. 10, no peak is observed at 562 nm demonstrating that the abs peak at 562 nm observed for ACI-24 liposomes is due to the presence of peptide.

Figure 11:
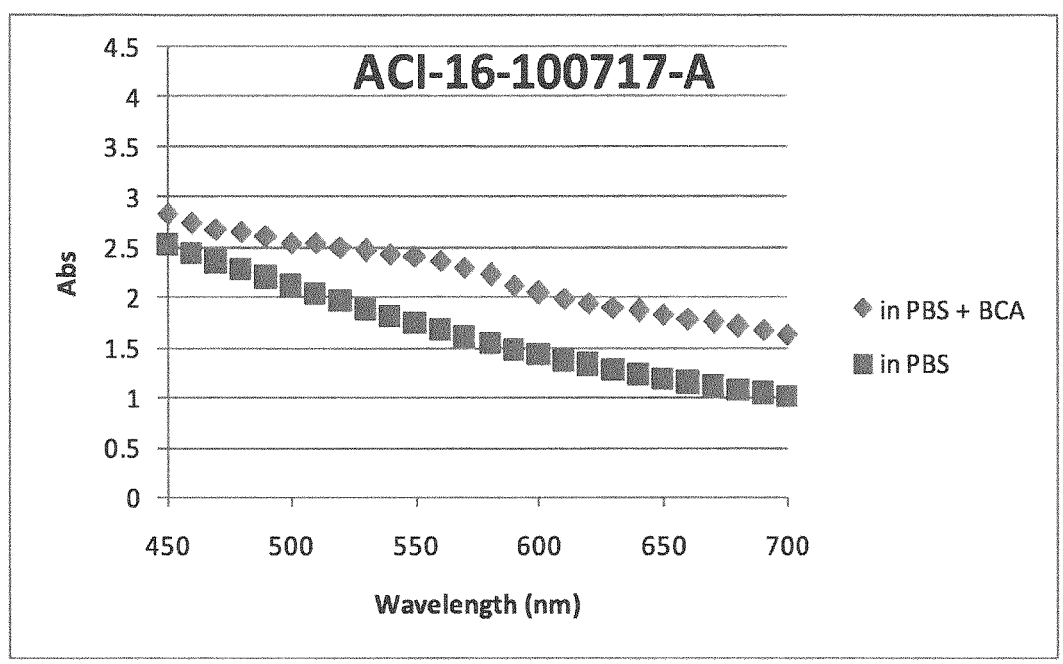
FIG. 11 shows absorbance spectra of liposomes containing only encapsulated Ac1-15 peptide (vaccine ACI-16).

8.4.2.4 Specificity for Peptide Only on Outer Membrane:

In order to test whether the BCA assay performed with liposomes diluted with PBS specifically reacts only with peptide present on the outer liposome membrane, the assay was performed with a batch of liposomes containing encapsulated water-soluble peptide Ac1-15 (ACI-16). As can be seen in FIG. 11, essentially no peak is observed at 562 nm, thus confirming that the BCA reaction occurs only for peptide exposed on the bilayer outer surface.

8.4.3 Precision

To assess the assay precision triplicate analyses were performed a batch of ACI-24 prepared with process L15 (ACI-24-100316-A). The results show that the absorbance readings in both PBS and SDS have coefficient of variations (CV's) of 1.77% and 0.57% respectively (Table 13).

8.4.4 Batch Analyses

Comparison of Liposomes Prepared with Different Processes

Figure 12:
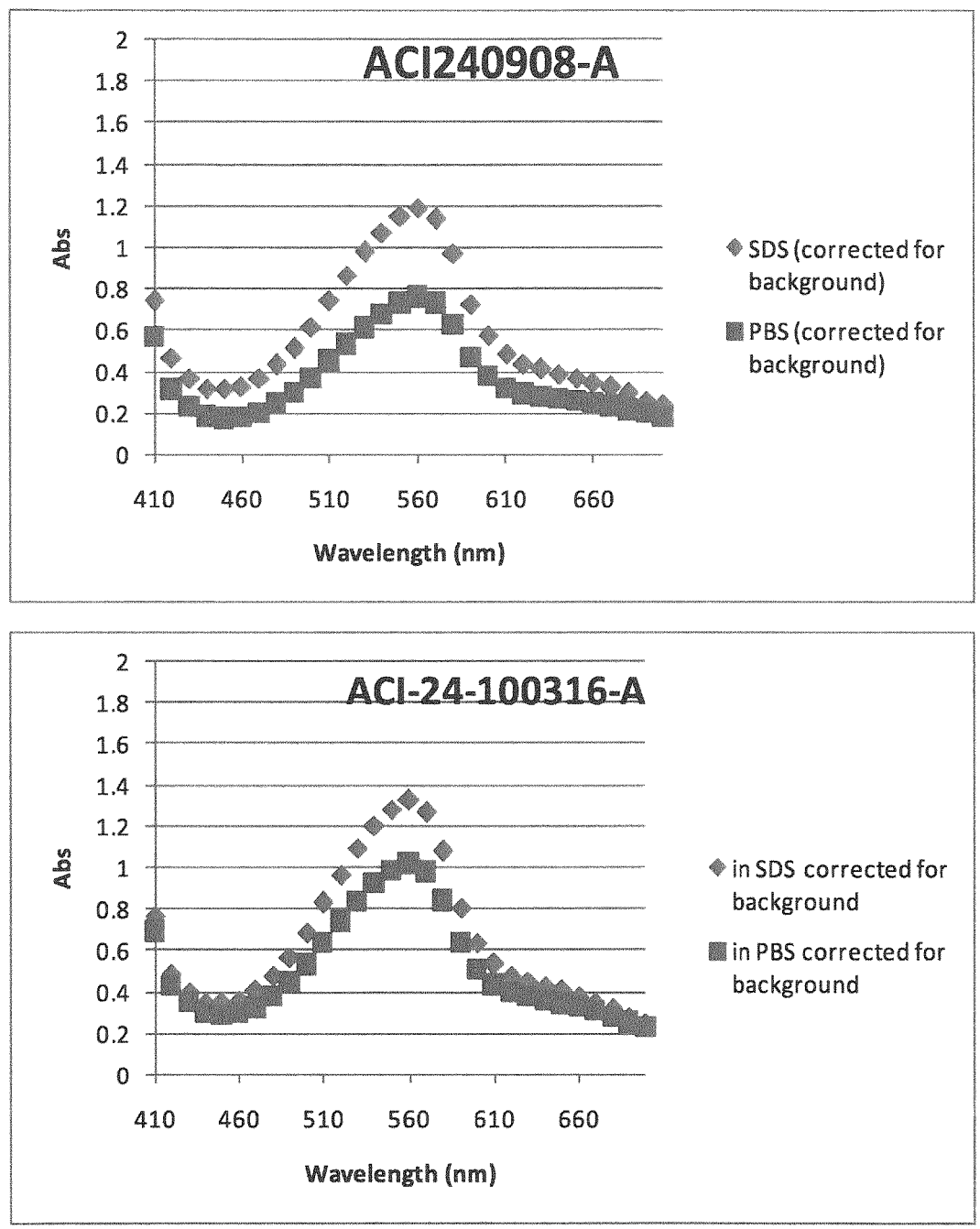
FIG. 12 shows comparison of absorbance spectra for batches of ACI-24 prepared with process D (ACI240908-A) or process L15 (ACI-24-100316-A).

Different batches of ACI-24 were analyzed in order to determine the effect of different liposome production processes upon the membrane topology of the peptide in the liposomes. The absorbance spectra of selected batches are shown in FIG. 12 and summarized in Table 14.

The results provided in Table 14 demonstrate the process flexibility" in terms of volumes,
adjuvants (more than one adjuvant),
antigens (more than one antigen),
lipid compositions
that may be used in the process of the invention.

Implementation of the assay for batch analyses revealed that liposomes prepared by different processes have different proportions of peptide present on the outer membrane surface. In particular, liposomes prepared with process L15 were found to display close to 30% more peptide on the outer surface than those prepared with the thin-film process A.

While the invention has been illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below.

The invention also covers all further features shown in the Figures individually although they may not have been described in the afore or following description.

Tables

TABLE 1

ACI-24-100316-A

| Characteristic | Test Method | Results |
| --- | --- | --- |
| Apperance | Visual inspection | White, milky suspension |
| Content Pal1-15 | HPLC | 424 ug/ml |
| Content membrane bound Pal1-15 | HPLC | 98% |
| Content MPLA | HPLC | 101 ug/ml |
| Congener A | HPLC | 99 ug/ml |
| Congener B | HPLC | 2 ug/ml |
| Size | DLS | 110 nm |
| Polydispersity | DLS | 0.25 |

TABLE 2

ACI-24-100316-B

| Characteristic | Test Method | Results |
| --- | --- | --- |
| Apperance | Visual inspection | White, milky suspension |
| Content Pal1-15 | HPLC | 482 ug/ml |
| Content membrane bound Pal1-15 | HPLC | 110% |
| Content MPLA | HPLC | 103 ug/ml |
| Congener A | HPLC | 100 ug/ml |
| Congener B | HPLC | 3 ug/ml |
| Size | DLS | 110 nm |
| Polydispersity | DLS | 0.25 |

TABLE 3

ACI-24-100316-C

| Characteristic | Test Method | Results |
| --- | --- | --- |
| Apperance | Visual inspection | White, milky suspension |
| Content Pal1-15 | HPLC | 406 ug/ml |
| Content membrane bound Pal1-15 | HPLC | 93% |

TABLE 3-continued

ACI-24-100316-C

| Characteristic | Test Method | Results |
|---|---|---|
| Content MPLA | HPLC | 102 ug/ml |
| Congener A | HPLC | 99 ug/ml |
| Congener B | HPLC | 3 ug/ml |
| Size | DLS | 110 nm |
| Polydispersity | DLS | 0.25 |

TABLE 4

ACI-24-091127-A

| Characteristic | Test Method | Results |
|---|---|---|
| Apperance | Visual inspection | White, milky suspension |
| Content Pal1-15 | HPLC | 647 ug/ml |
| Content membrane bound Pal1-15 | HPLC | 73% |
| Content MPLA | HPLC | 250 ug/ml |
| Congener A | HPLC | 214 ug/ml |
| Congener B | HPLC | 36 ug/ml |
| Size | DLS | 109 nm |
| Polydispersity | DLS | 0.9 |

TABLE 5

ACI-24-091127-B

| Characteristic | Test Method | Results |
|---|---|---|
| Apperance | Visual inspection | White, milky suspension |
| Content Pal1-15 | HPLC | 543 ug/ml |
| Content membrane bound Pal1-15 | HPLC | 88% |
| Content MPLA | HPLC | 884 ug/ml |
| Congener A | HPLC | 818 ug/ml |
| Congener B | HPLC | 66 ug/ml |
| Size | DLS | 117 nm |
| Polydispersity | DLS | 0.30 |

TABLE 6

ACI-33-091127

| Characteristic | Test Method | Results |
|---|---|---|
| Apperance | Visual inspection | White, milky suspension |
| Content T1 | HPLC | 348 ug/ml |
| Content membrane bound T1 | HPLC | 87% |
| Content MPLA | HPLC | 96 ug/ml |
| Congener A | HPLC | 81 ug/ml |
| Congener B | HPLC | 15 ug/ml |
| Size | DLS | 106 nm |
| Polydispersity | DLS | 0.18 |

TABLE 7

ACI-33-091808-A

| Characteristic | Test Method | Results |
|---|---|---|
| Apperance | Visual inspection | White, milky suspension |
| Content T1 | HPLC | 63 ug/ml |

TABLE 7-continued

ACI-33-091808-A

| Characteristic | Test Method | Results |
|---|---|---|
| Content membrane bound T1 | HPLC | ND |
| Content MPLA | HPLC | 79 ug/ml |
| Congener A | HPLC | 79 ug/ml |
| Congener B | HPLC | 0 ug/ml |
| Size | DLS | ND |
| Polydispersity | DLS | ND |

TABLE 8

ACI-35-091127

| Characteristic | Test Method | Results |
|---|---|---|
| Apperance | Visual inspection | White, milky suspension |
| Content T3 | HPLC | 321 ug/ml |
| Content membrane bound T3 | HPLC | 109% |
| Content MPLA | HPLC | 101 ug/ml |
| Congener A | HPLC | 96 ug/ml |
| Congener B | HPLC | 5 ug/ml |
| Size | DLS | 102 nm |
| Polydispersity | DLS | 0.25 |

TABLE 9

ACI-35-0910820-A

| Characteristic | Test Method | Results |
|---|---|---|
| Apperance | Visual inspection | White, milky suspension |
| Content T3 | HPLC | 61 ug/ml |
| Content membrane bound T3 | HPLC | ND |
| Content MPLA | HPLC | 141 ug/ml |
| Congener A | HPLC | 141 ug/ml |
| Congener B | HPLC | 0 ug/ml |
| Size | DLS | ND |
| Polydispersity | DLS | ND |

TABLE 10

ACI-41-100531

| Characteristic | Test Method | Results |
|---|---|---|
| Apperance | Visual inspection | White, milky suspension |
| Content T8 | HPLC | 362 ug/ml |
| Content T9 | HPLC | 189 ug/ml |
| Content MPLA | HPLC | 93 ug/ml |
| Congener A | HPLC | 88 ug/ml |
| Congener B | HPLC | 5 ug/ml |
| Size | DLS | 79 nm |
| Polydispersity | DLS | 0.25 |

TABLE 11

ACI-24 process D#1

| Characteristic | Test Method | Results |
|---|---|---|
| Apperance | Visual inspection | White, milky suspension |
| Content Pal1-15 | HPLC | 388 ug/ml |

TABLE 11-continued

ACI-24 process D#1

| Characteristic | Test Method | Results |
|---|---|---|
| Content membrane bound Pal1-15 | HPLC | ND |
| Content MPLA | HPLC | 58 ug/ml |
| Congener A | HPLC | 12 ug/ml |
| Congener B | HPLC | 46 ug/ml |
| Size | DLS | 115 nm |
| Polydispersity | DLS | 0.14 |

TABLE 12

ACI-24 process D#2

| Characteristic | Test Method | Results |
|---|---|---|
| Apperance | Visual inspection | White, milky suspension |
| Content Pal1-15 | HPLC | 375 ug/ml |
| Content membrane bound Pal1-15 | HPLC | ND |
| Content MPLA | HPLC | 52 ug/ml |
| Congener A | HPLC | 11 ug/ml |
| Congener B | HPLC | 41 ug/ml |
| Size | DLS | 105 nm |
| Polydispersity | DLS | 0.15 |

TABLE 13

| Sample conditions | Abs 1 | Abs 2 | Abs 3 | Average | S.D. | CV (%) |
|---|---|---|---|---|---|---|
| SDS with BCA | 1.174 | 1.152 | 1.157 | | | |
| SDS without BCA | 0.052 | 0.042 | 0.045 | | | |
| Difference | 1.122 | 1.110 | 1.112 | 1.115 | 0.006 | 0.57 |
| PBS with BCA | 1.315 | 1.313 | 1.281 | | | |
| PBS without BCA | 0.464 | 0.454 | 0.451 | | | |
| Difference | 0.852 | 0.859 | 0.830 | 0.847 | 0.015 | 1.77 |

TABLE 14

| Production Process | Peptide added before or after liposome formation | Batch name | Relative Peptide on outer membrane (%) | Size (nm) | MPLA Hydrlosis | Filterability | Scalable | Process Flexibility | Antigen added after liposome formation | Adjuvant added after liposome formation |
|---|---|---|---|---|---|---|---|---|---|---|
| A (thin-film) as described in WO2007/068411 | Before | ACI-24-090813-A | 54 | >500 nm | No | No | No | Low | No | No |
| D (cross-flow ethanol injection) | Before | ACI240108-B | 62 | 96 | Yes | Yes | Yes | Low | No | No |
| | | ACI240709-A | 58 | 115 | Yes | Yes | Yes | Low | No | No |
| | | ACI241008-A | 67 | 97 | Yes | Yes | Yes | Low | No | No |
| | | ACI240908-A | 64 | 105 | Yes | Yes | Yes | Low | No | No |
| L15 | After | ACI-24-091016-B | 81 | 116 | No | Yes | Yes | High | Yes | No |
| | | ACI-24-100316-A | 81 | 110 | No | Yes | Yes | High | Yes | No |
| L16 | After | ACI-24-091127-A | 82 | 109 | No | Yes | Yes | High | Yes | Yes |
| | | ACI-24-091127-B | 84 | 117 | No | Yes | Yes | High | Yes | Yes |
| | | ACI-24-100317-C | 72 | 113 | No | Yes | Yes | High | Yes | Yes |
| L20 | After | ACI001J | 84 | 101 | No | Yes | Yes | High | Yes | No |

"Process Flexibility" means that the process can be used for various
volumes,
adjuvants (more than one adjuvant),
antigens (more than one antigen),
lipid compositions.

REFERENCE LIST

Allen et al., Cellular & Molecular Biology Letters, 2002, 7, 217-219
Allison and Gregoriadis, Nature, 1974, 252, 252
Alving et al., Immunol Rev 1995; 145:5
Frisch, Eur J Immunol 1991; 21:185
Gill et al., Nature Med. 9: 589-595 (2003)
Guan et al., Bioconjugate Chem, 1998, 9, 451-458
Harlow and Lane, Antibodies: A Laboratory Manual (Cold Spring Harbor Laboratory, New York 1988 555-612
Hodgson et al., Bio/Technoloy, 9:421 (1991)
Huang et al., 1997, Carcinogenesis 18, 83-88
IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata, updates compiled by A. Jenkins.
Kennedy, J. H., et al., 1976 (Clin. Chim. Acta 70:1-31)
Kersten and Crommelin, Biochimica et Biophysica Acta 1995, 1241, 117-138
Khaw, B. A. et al. J. Nucl. Med. 23:1011-1019 (1982)

Moreira et al., Pharmaceutical Research, 2002, 19, 265-269
Muhs et al., PNAS, 2007, 104, 9810-9810
Neuwelt, E. A., Implication of the Blood-Brain Barrier and its Manipulation, Vols 1 & 2, Plenum Press, N.Y. (1989))
Nicolau et al., PNAS, 2002, 99, 2332-2337; WO2007/068411
Queen et al., Proc. Natl. Acad Sci USA, 86:10029-10032 (1989)
Papanastassiou et al., Gene Therapy 9: 398-406 (2002)
Rousseaux et al. Methods Enzymology, 121:663-69, Academic Press, 1986
Schurs, A. H. W. M., et al. 1977 (Clin. Chim Acta 57:1-40)
Torchilin, Nature Reviews, 2005, 4, 145-160
Weiss, R. B., et al., Drugs, 46(3): 360-377 (1993)
Zrein et al. (1998), Clinical and Diagnostic Laboratory Immunology, Vol. 5, No. 1: 45
Patent Literature:
U.S. Pat. Nos. 5,855,866, 5,965,132, 6,261,535, 6,051,230 and 6,451,312
U.S. Pat. Nos. 6,093,399, 6,004,555, 5,877,289, and 6,036,955
U.S. Pat. Nos. 5,112,596, 5,268,164, 5,506,206, and 5,686,416
U.S. Pat. No. 5,004,697
U.S. Pat. No. 5,620,689
U.S. Pat. No. 5,620,689
US20020065259, 2003/0162695, and 2005/0124533
US 20100119444
US20020038086
US20020025313
US20030083299
US20030229013
US20030073713
US20030129186
US20030229013
US20050089473
WO96/13590
WO96/29605
WO 2004/058258
WO 2007/068411

---

The invention claimed is:

1. A method of preparing a liposome-based construct comprising a peptide modified through hydrophobic moieties reconstituted in a liposome, comprising the steps of
    (i) preparing liposomes in a solution;
    (ii) preparing a modified peptide by adding to the N- and/or C-terminus of the peptide molecule at least one hydrophobic moiety;
    (iii) solubilizing the modified peptide in the presence of a surfactant such that the modified peptide is in a micellar form;
    (iv) loading the prepared liposomes of step (i) by adding the solubilized modified peptide to the prepared liposomes and diluting the solubilized modified peptide below a critical micellar concentration of the surfactant such that the micellar form of the modified peptide is disrupted thereby driving integration of the hydrophobic moieties of the modified peptide into an external layer of the preformed liposomes such that at least 72%, 80%, 90%, or 100% of said peptide is present on the outer surface of the liposome.

2. The method of claim 1, further comprising loading the preformed liposomes with an adjuvant, wherein the adjuvant loading is carried out (a) prior to, (b) together with, or (c) after the loading of the liposomes with the diluted solubilized antigenic peptide.

3. The method of claim 1, wherein the peptide is modified by:
    (a) addition of a fatty acid, a triglyceride, a diglyceride, a steroid, a sphingolipid, a glycolipid, a phospholipid, or a combination thereof;
    (b) at least 2 palmitoylated amino acid residues covalently attached to the N- and C-terminus of the peptide, respectively; or
    (c) at least 4 palmitoylated amino acid residues, two of which are covalently attached to the N- and C-terminus of the peptide, respectively.

* * * * *